(12) United States Patent
Ota et al.

(10) Patent No.: US 7,809,416 B2
(45) Date of Patent: Oct. 5, 2010

(54) METHOD OF PREPARING CALIBRATION CURVE FOR QUANTITATIVE ANALYSIS OF IN-VIVO COMPONENT, AND QUANTITATIVE ANALYZER USING THE CALIBRATION CURVE

(75) Inventors: Tomohiro Ota, Takarazuka (JP); Katsuhiro Hirata, Sanda (JP); Katsuhiko Maruo, Itami (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 1037 days.

(21) Appl. No.: 11/210,855

(22) Filed: Aug. 25, 2005

(65) Prior Publication Data
US 2006/0063987 A1 Mar. 23, 2006

(30) Foreign Application Priority Data
Aug. 25, 2004 (JP) ............................. 2004-245782

(51) Int. Cl.
*A61B 5/1455* (2006.01)
(52) U.S. Cl. ...................................... 600/316; 600/310
(58) Field of Classification Search ......... 600/309–344; 382/115
See application file for complete search history.

(56) References Cited

U.S. PATENT DOCUMENTS

| | | | |
|---|---|---|---|
| 4,655,225 A | | 4/1987 | Dahne et al. |
| 5,533,509 A | | 7/1996 | Koashi et al. |
| 5,957,841 A | | 9/1999 | Maruo et al. |
| 6,157,041 A | * | 12/2000 | Thomas et al. ............... 250/573 |
| 6,181,957 B1 | * | 1/2001 | Lambert et al. ............. 600/319 |
| 6,622,032 B1 | * | 9/2003 | Robinson et al. ............ 600/310 |
| 7,203,345 B2 | * | 4/2007 | Rowe et al. .................. 382/115 |
| 2003/0023148 A1 | | 1/2003 | Lorenz et al. |
| 2003/0216627 A1 | | 11/2003 | Lorenz et al. |
| 2004/0033618 A1 | | 2/2004 | Haass et al. |

(Continued)

FOREIGN PATENT DOCUMENTS

JP 2003-050200 A 2/2003

(Continued)

OTHER PUBLICATIONS

Arnold et al., Phatom Glucose Calibration . . . , Anal. Chem. 1998,70, 1773-1781.*

(Continued)

*Primary Examiner*—Eric F Winakur
(74) *Attorney, Agent, or Firm*—Cheng Law Group, PLLC

(57) ABSTRACT

A method of non-invasively determining a concentration of an in-vivo component such as blood sugar level (glucose) of a subject is provided. An absorption spectrum of the subject is measured by use of near-infrared light. The concentration of the in-vivo component is determined by use of the absorption spectrum of the subject and a calibration curve. The calibration curve is prepared by determining a plurality of difference absorption spectra that are differences between a plurality of near-infrared absorption spectra of a living body and a reference absorption spectrum selected from the near-infrared absorption spectra, determining a plurality of synthetic absorption spectra, which are obtained by synthesizing each of the difference absorption spectra with a previously measured reference absorption spectrum of the subject, and performing a multivariate analysis with use of the obtained synthetic absorption spectra.

3 Claims, 15 Drawing Sheets

U.S. PATENT DOCUMENTS

| | | |
|---|---|---|
| 2004/0142402 A1 | 7/2004 | Maruo et al. |
| 2006/0063983 A1 | 3/2006 | Yamakoshi |
| 2008/0171924 A9* | 7/2008 | Ridder et al. ............... 600/310 |

FOREIGN PATENT DOCUMENTS

| | | |
|---|---|---|
| JP | 2003-144421 A | 5/2003 |
| JP | 2004-138454 A | 5/2004 |
| WO | WO-95/05120 A1 | 2/1995 |
| WO | WO-03/079900 A1 | 10/2003 |
| WO | WO-04/000113 A1 | 12/2003 |

OTHER PUBLICATIONS

Shaw et al., Infrared Spectroscopy . . . , J. Appl. Physiol. 1996, 81, 2328-2335.*

Hahn et al., Reagantless Determination of Human . . . , Dec. 2003, V 7(4), 240-244.*

Bittner et al., Investigation of Experimental Errors . . . , J. of Molecular Structure 348 (1995) 21-24.*

European Search Report Dated Dec. 23, 2005.

Decision to Grant a Patent for the Application No. 2005-244785 from Japan Patent Office mailed Aug. 10, 2010.

* cited by examiner

S30
Measurement of a plurality of sets of blood sugar level and absorption spectra in first and second wavelength regions

S31
Baseline compensation by subtracting the absorption spectrum in the second wavelength region from the absorption spectrum in the first wavelength region

S32
Determination of reference absorption spectrum

S33
Calculation of difference absorption spectra between the reference absorption spectrum and each of the baseline-compensated absorption spectra

S34
Preparation of calibration curve by multivariate analysis

FIG. 13

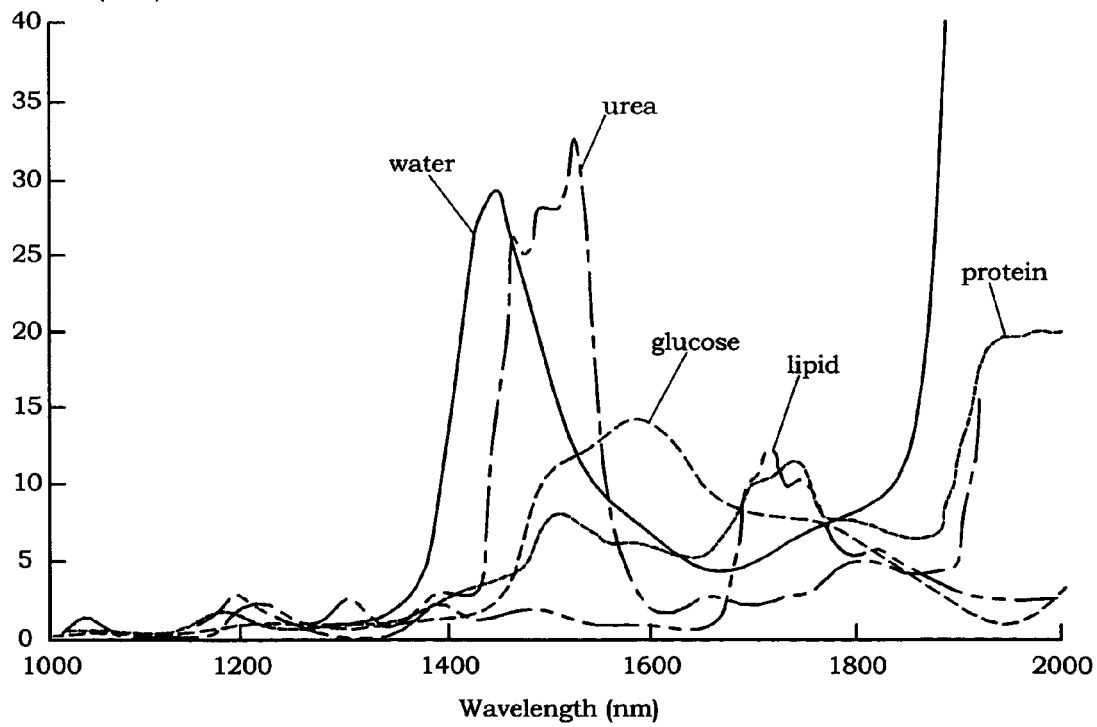

FIG. 14

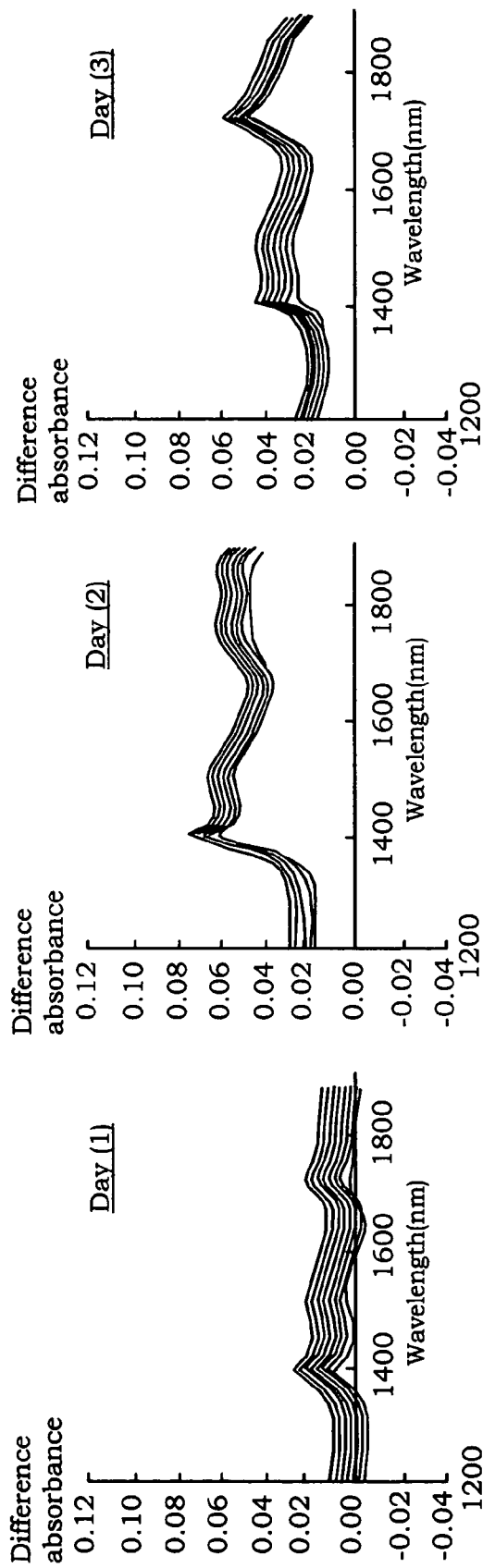
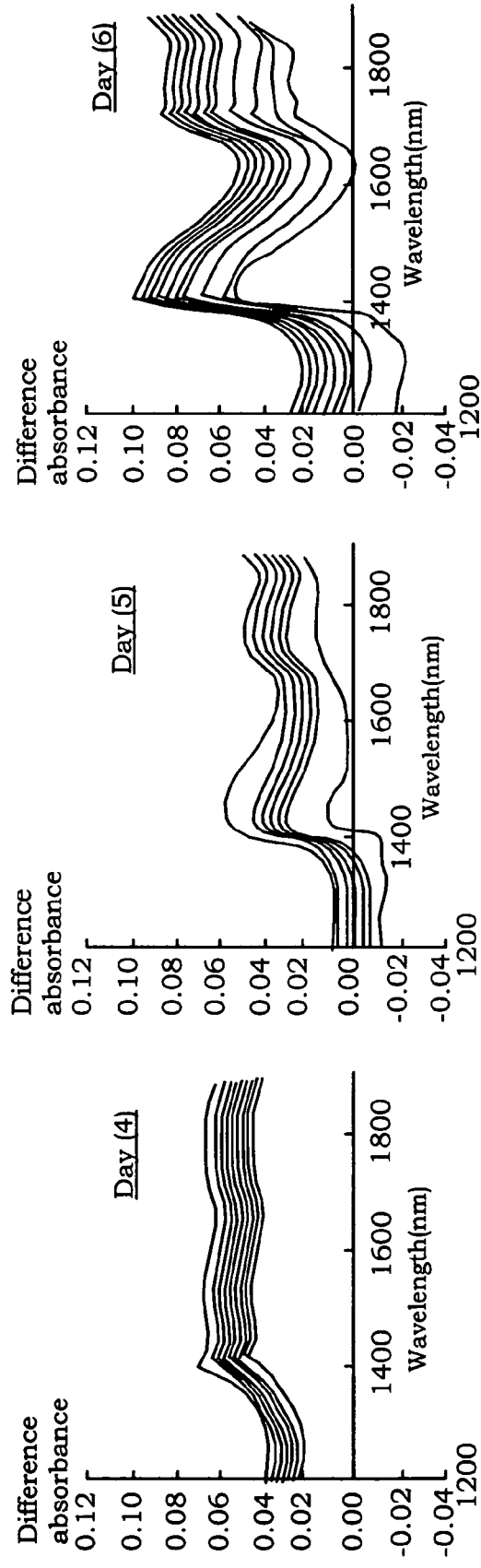
FIG. 15A Day (1)
FIG. 15B Day (2)
FIG. 15C Day (3)
FIG. 15D Day (4)
FIG. 15E Day (5)
FIG. 15F Day (6)

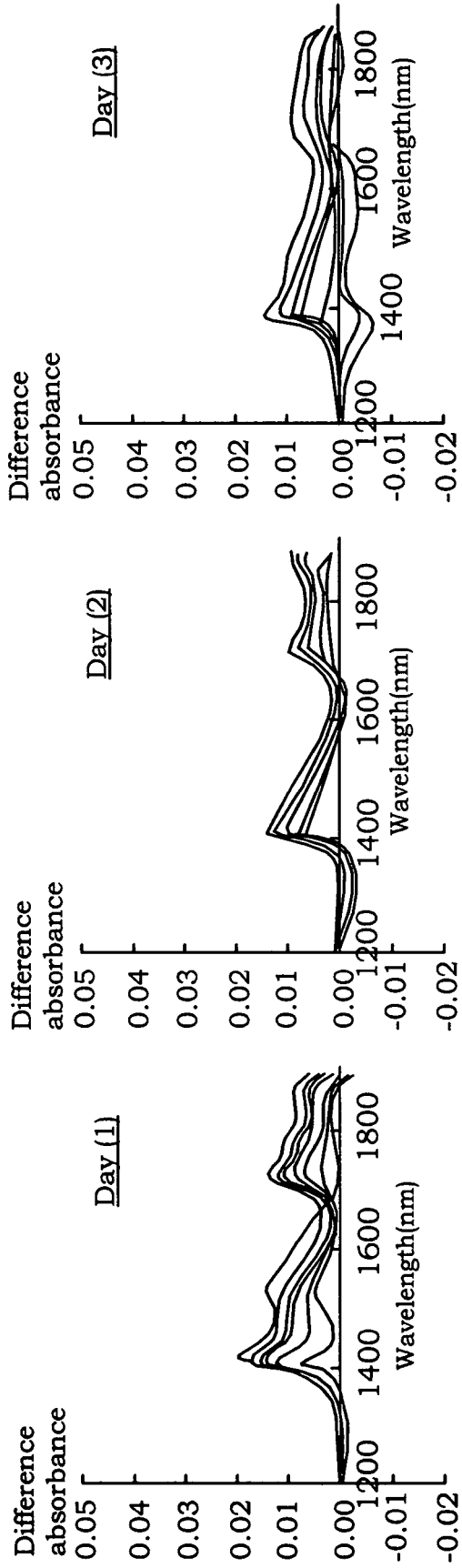
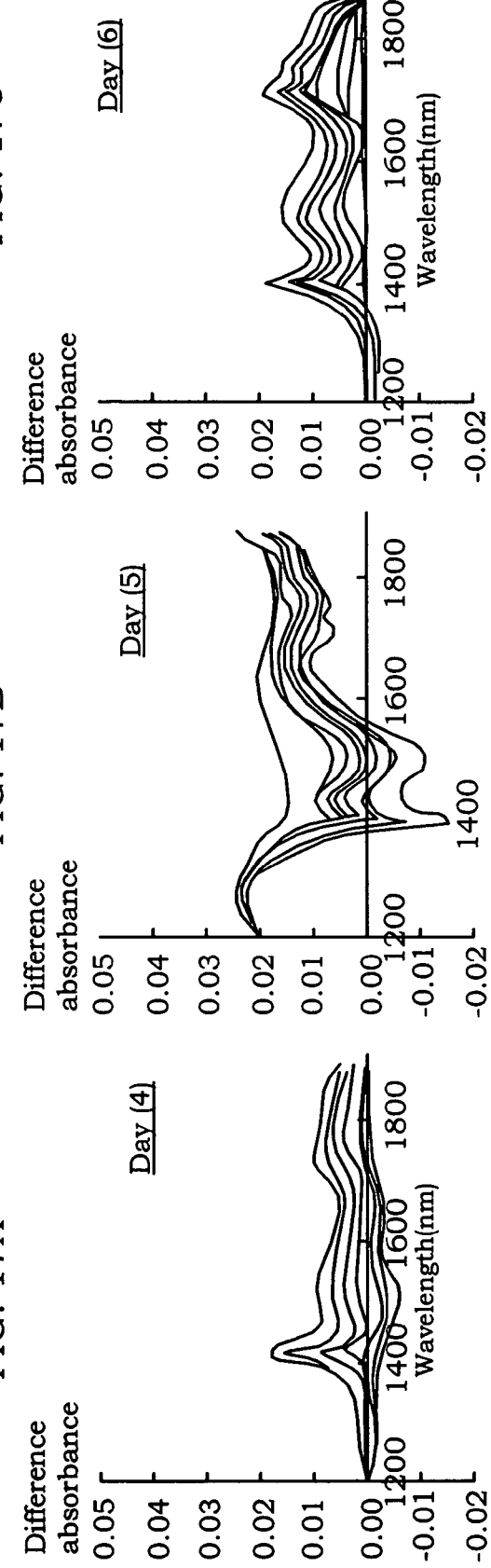
FIG. 17A  FIG. 17B  FIG. 17C
FIG. 17D  FIG. 17E  FIG. 17F

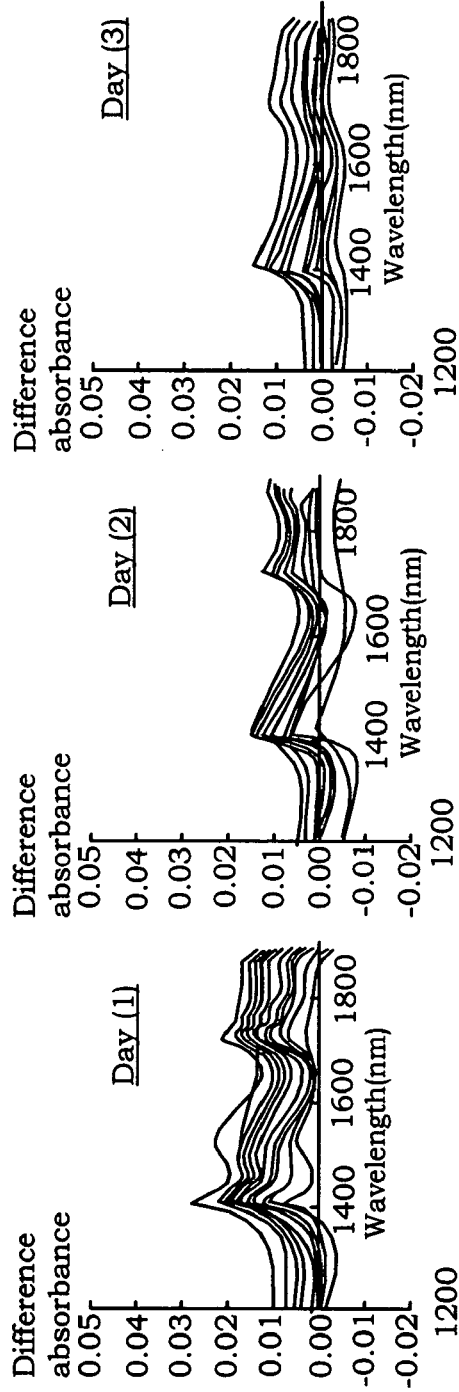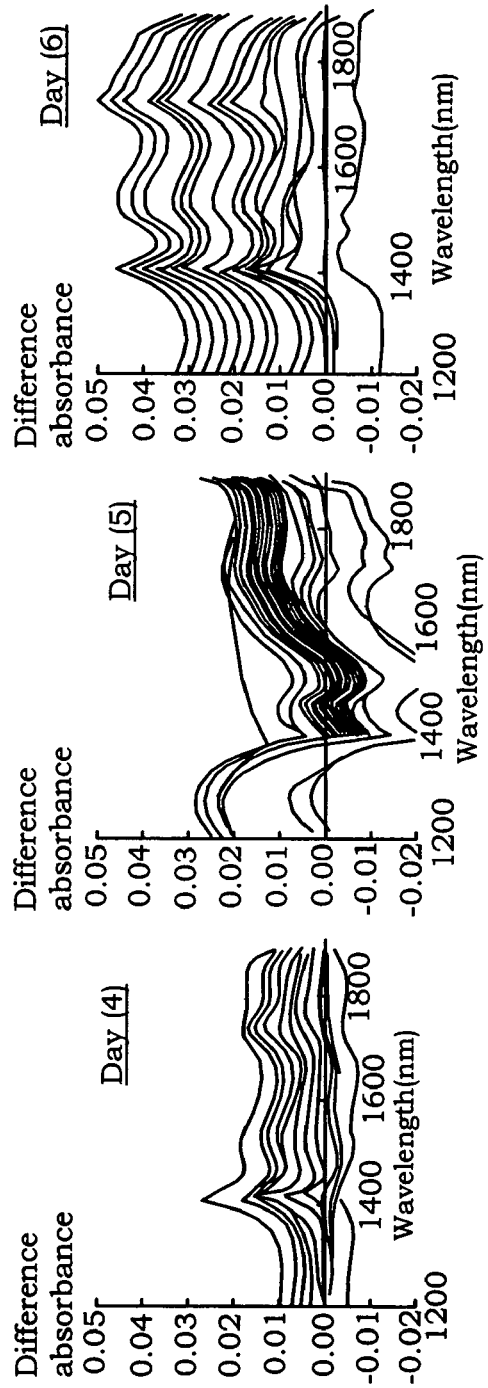
FIG. 19A  FIG. 19B  FIG. 19C
FIG. 19D  FIG. 19E  FIG. 19F

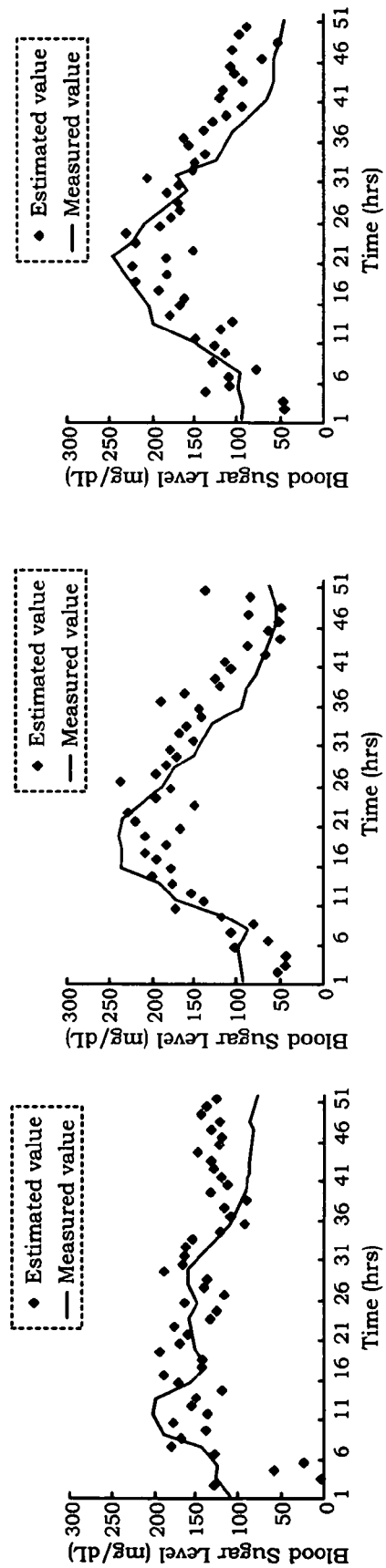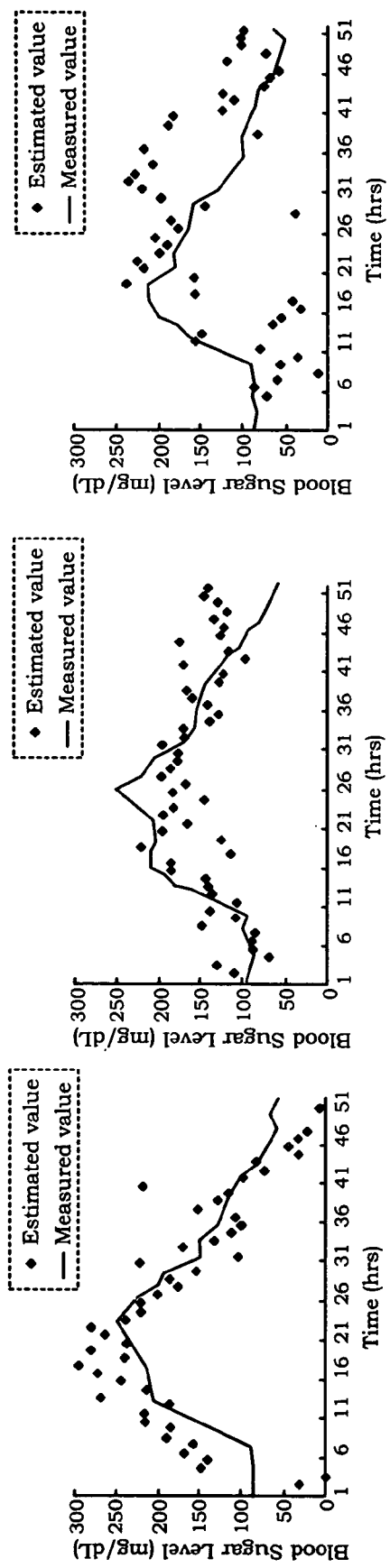
FIG. 20A
FIG. 20B
FIG. 20C
FIG. 20D
FIG. 20E
FIG. 20F

METHOD OF PREPARING CALIBRATION CURVE FOR QUANTITATIVE ANALYSIS OF IN-VIVO COMPONENT, AND QUANTITATIVE ANALYZER USING THE CALIBRATION CURVE

BACKGROUND OF THE INVENTION

1. Field of the Invention

The present invention relates to a technique of non-invasively estimating a concentration of an in-vivo component such as blood sugar level (glucose).

2. Disclosure of the Prior Art

For health controls and medical treatments, attention has been given to a method of non-invasively analyzing an in-vivo component such as glucose, protein, lipid, water or urea without blood drawing. When using near-infrared light in this analyzing method, there are advantages that an aqueous solution can be analyzed because an absorption spectrum of water in the near-infrared region is small, and also the near-infrared light is easy to propagate in the living body. On the contrary, since a signal level in the near-infrared region is much smaller than the signal level in a mid-infrared region, and also an absorption signal of the target in-vivo component such as glucose is susceptible to concentration changes of other in-vivo components such as water, lipid and protein, it was difficult to accurately analyze the target in-vivo component by using the peak position or the peak height.

In recent years, to improve these inconveniences in the near-infrared spectroscopic analysis, it has been proposed to use a multivariate analysis such as PLS regression analysis. In this case, even when an absorption signal in the near-infrared region is of a poor S/N ratio, or concentration changes of the other in-vivo components occur, a practical quantitative analysis using the near-infrared light becomes possible.

For example, U.S. Pat. No. 5,957,841 discloses a method of determining a glucose concentration in a target by using near-infrared spectroscopy. In this method, a near-infrared radiation is projected on a skin of a subject, and then a resultant radiation from the skin is received by an optical fiber bundle. A spectrum analysis of the received radiation is performed to detect absorption signals from a first wavelength region (e.g., 1550 to 1650 nm) having an absorption peak of OH group derived from glucose molecule, second wavelength region (e.g., 1480 to 1550 nm) having an absorption peak of NH group, and a third wavelength region (e.g., 1650 to 1880 nm) having an absorption peak of CH group. The glucose concentration is determined by multivariate analysis with use of the absorption signals as explanatory variables.

In addition, Japanese Patent Early Publication [kokai] No. 2003-50200 discloses a method of determining the concentration of a target component in a medium according to a stochastic simulation. In this method, light paths in the medium are analyzed by the stochastic simulation such as Monte Carlo method. In addition, a dada table is prepared, which presents a change in diffuse reflectance in the case of changing absorption coefficient and reduced scattering coefficient as optical characteristics of the medium in required ranges, and then a smoothing treatment for the diffuse reflectance is performed by means of a regression analysis to prepare a compensated data table. Next, an actually measured spectrum is obtained by irradiating light such as near-infrared light in a wavelength region of 1000 to 2500 nm to the medium, and detecting a resultant radiation therefrom, and compared with a reference spectrum provided from the compensated data table to determine the concentration of the target component in the medium. In addition, it is disclosed that when calculating a spectrum change caused by a concentration change of a component other than the target component in the medium from the compensated data table, the target component can be determined from the actually measured spectrum by the multivariate analysis such as multiple linear regression (MLR) analysis or principal component regression (PCR) analysis.

However, it is known that a skin of the living body, to which the near-infrared light is irradiated, usually has a nonuniform structure, and there are differences among individuals in thickness of the skin and the skin structure. In addition, the concentration of the target in-vivo component of a subject measured in the morning of a day is often different from the concentration of the subject measured in the evening of the same day. Thus, concentration fluctuations within one day of the target in-vivo component and another in-vivo components having an influence on the concentration of the target in-vivo component of the subject lead to reduction in estimation accuracy of the target in-vivo component.

FIG. 5A shows measurement results of the relation between blood sugar level as the target in-vivo component and the concentration of the other in-vivo component with respect to each of three subjects (A, B, C). In this figure, ellipses (A1, A2, A3, A4) present the measurement results of the subject A in different days. Similarly, ellipses (B1, B2, B3) present the measurement results of the subject B in different days, and ellipses (C1, C2, C3) present the measurement results of the subject C in different days. In addition, plots "m" in each of the ellipses show fluctuations within one day of the measurement values of the respective subject. In this case, since there is a data poor region G, as shown by a dotted line in FIG. 5A, it is difficult to obtain high estimation accuracy at the region G by a calibration curve prepared from the measurement results of FIG. 5A.

Therefore, to provide stable reliability of the estimation accuracy of the target in-vivo component, it is desired to prepare the calibration curve by use of larger amounts of data. However, it leads to a considerable increase in time required for data collection. Additionally, when glucose, i.e., blood sugar level is selected as the target in-vivo component, an absorption signal of glucose is very weak. Therefore, even when the data amounts used are increased, there is a fear that a sufficient improvement of the estimation accuracy is not achieved by the influence of noise components.

SUMMARY OF THE INVENTION

Therefore, a primary concern of the present invention is to provide a method of preparing a calibration curve for quantitative analysis, by use of which the concentration of an ever-changing target in-vivo component such as glucose can be estimated with stable accuracy. That is, the method of the present invention comprises the steps of determining a plurality of difference absorption spectra, which are differences between a plurality of near-infrared absorption spectra of a living body and a reference absorption spectrum, and performing a multivariate analysis with use of the difference absorption spectra to prepare the calibration curve.

According to the present invention, by using the difference absorption spectra in the multivariate analysis, it is possible to remove the influences of differences among individuals in living tissue, variations in measurement sites, a change in the living tissue on scattering phenomena, and fluctuations in absorption spectrum of the target in-vivo component caused by a change in concentration of the other in-vivo component, and consequently achieve improved estimation accuracy of the concentration of the target in-vivo component.

In the above method, it is preferred that the near-infrared absorption spectra are measured by irradiating near-infrared light to the living body and performing a spectrum analysis of a resultant radiation from the living body.

In the above method, it is preferred that the difference absorption spectra are obtained according to a light propagation simulation, which is defined as a method of analyzing a light propagation in a simulated living body. In this case, the calibration curve can be prepared without using an apparatus for actually measuring the near-infrared absorption spectra from the living body. In addition, since there is no influence of noise components in the simulation, it is possible to prepare a calibration curve with a high reliability in estimation accuracy even when the in-vivo component such as glucose, which provides a very weak absorption signal, is the target in-vivo component.

In the above method, it is preferred that the reference absorption spectrum is selected from the near-infrared absorption spectra. In addition, when the near-infrared absorption spectra are measured in different days, it is preferred that the reference absorption spectrum is selected from the near-infrared absorption spectra measured in each of the different days.

As a preferred embodiment of the present invention, the calibration curve is prepared by performing the multivariate analysis with use of a plurality of synthetic absorption spectra, which are obtained by synthesizing each of the difference absorption spectra with a second reference absorption spectrum different from the reference absorption spectrum described above. For example, when the calibration curve is used in the quantitative analysis for a subject, the second reference absorption spectrum is a previously measured near-infrared absorption spectrum of the subject. Alternatively, when a plurality of near-infrared absorption spectra of the subject are previously measured, its average may be used as the second reference absorption spectrum. In this case, since concentration fluctuations within one day of the target in-vivo component of the subject is considered in the synthetic absorption spectra, the quantitative analysis can be more accurately performed by use of the calibration curve peculiar to the subject.

As another preferred embodiment of the present invention, the method described above further comprises the steps of measuring a concentration of the target in-vivo component from the living body by means of, for example, collection of blood, at the time of measuring each of the near-infrared absorption spectra, and determining a plurality of difference concentrations, each of which is a difference between the concentration of the in-vivo component and a reference concentration. For example, the reference concentration is selected from the measured concentrations of the target in-vivo component. In this case, the calibration curve is prepared by performing the multivariate analysis with use of a difference data table composed of the difference concentrations and the difference absorption spectra.

To further improve the reliability of the calibration curve, it is preferred that the near-infrared absorption spectra are measured in a first wavelength region (e.g., 1200 nm~1880 nm) having a large absorption derived from glucose molecule and a second wavelength region (e.g., 1000 nm~1350 nm) having a relatively small absorption peculiar to water molecule and hemoglobin, and a baseline compensation of the near-infrared absorption spectra measured in the first wavelength region is performed before determining the difference absorption spectra by use of the near-infrared absorption spectra measured in the second wavelength region.

A further concern of the present invention is to provide a method of non-invasively determining a concentration of an in-vivo component of a subject. That is, this method comprises the steps of measuring a near-infrared absorption spectrum of the subject, and determining the concentration of the in-vivo component of the subject by use of the measured near-infrared absorption spectrum of the subject and the calibration curve prepared by the above-described method.

Another concern of the present invention is to provide a quantitative analyzer for non-invasively determining a concentration of an in-vivo component of a subject according to the method described above. That is, this analyzer comprises:

a light irradiating unit configured to irradiate near-infrared light to a skin of the subject;

a light receiving unit configured to receive a resultant radiation from the skin;

a memory for storing a calibration curve for quantitative analysis of the in-vivo component of the subject, which is prepared by determining a plurality of difference absorption spectra, which are differences between a plurality of near-infrared absorption spectra of a living body and a reference absorption spectrum, and performing a multivariate analysis with use of the difference absorption spectra; and an operation unit configured to calculate the concentration of the in-vivo component of the subject by use of an output of the light receiving unit and the calibration curve read out from the memory.

These and additional features and advantages of the present invention will become more apparent from preferred embodiments explained below, referring to the attached drawings.

BRIEF EXPLANATION OF THE DRAWINGS

FIG. 13 is a flowchart of method of preparing a calibration curve according to a fifth embodiment of the present invention;

FIG. 14 is a graph showing absorption spectra of in-vivo components;

FIGS. 15A to 15F are respectively graphs showing fluctuations within one day of absorption spectra measured at different days;

FIGS. 17A to 17F are respectively graphs showing fluctuations within one day of absorption characteristics obtained by performing a baseline compensation to absorption spectra measured at different days, and, then determining difference absorption spectra;

FIGS. 19A to 19F are respectively graphs showing fluctuations within one day of absorption characteristics obtained by determining difference absorption spectra from the absorption spectra measured at different days without the baseline compensation; and FIGS. 20A to 20F are respectively graphs showing comparisons between measured blood sugar levels and blood sugar levels estimated by use of the data of FIGS. 19A to 19F.

DETAIL DESCRIPTION OF PREFERRED EMBODIMENTS OF THE INVENTION

A method of preparing a calibration curve of the present invention, quantitative analysis of an in-vivo component of a subject using the calibration curve, and an apparatus used therefor are explained in detail according to the following preferred embodiments.

First Embodiment

Figure 1:
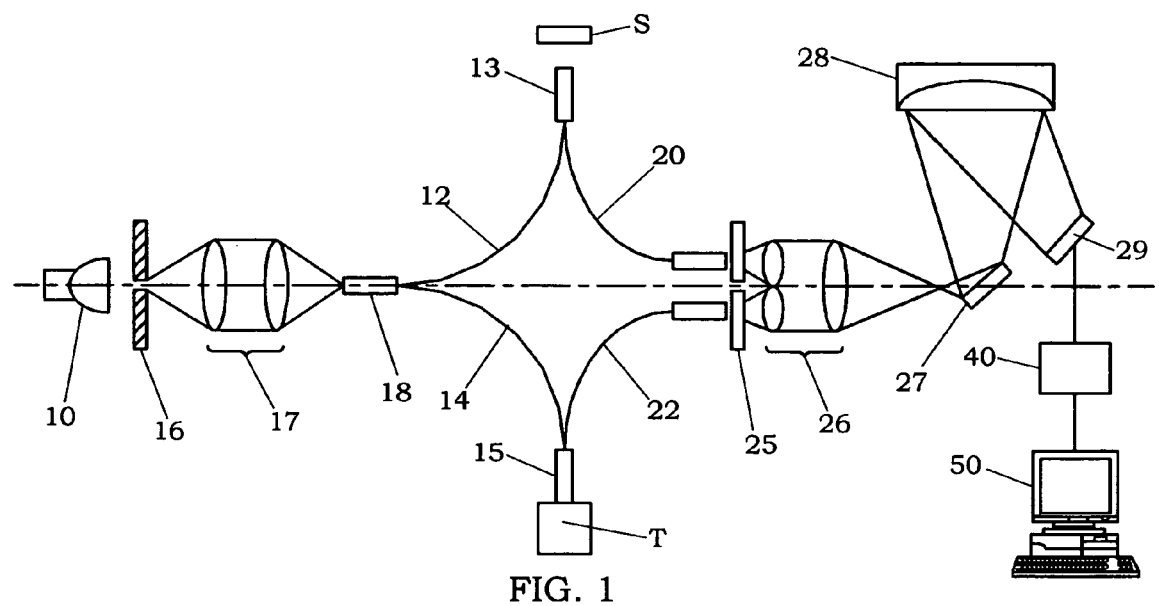
FIG. 1 is a schematic diagram of an apparatus for non-invasively performing a quantitative analysis of an in-vivo component according to a first embodiment of the present invention.

As shown in FIG. 1, an apparatus of this embodiment for non-invasively performing a quantitative analysis of an in-vivo component of a subject with use of near-infrared light comprises a light irradiating unit configured to irradiate the near-infrared light to an object such as a skin of the subject, light receiving unit configured to receive a resultant radiation from the object, memory storing a calibration curve prepared by the method described later, and an operation unit configured to calculate the concentration of the in-vivo component of the subject by use of an output of the light receiving unit and the calibration curve read out from the memory.

The light irradiating unit comprises a light source 10 such as a halogen lamp for emitting the near-infrared light, first optical-fibers 12, which have one ends connected to the light source 10 through an optional optical system and the other ends connected to a measurement probe 13 for projecting the near-infrared light on the skin "S" of the subject, and second optical fibers 14, which has one ends connected to the light source 10 through the optical system and the other ends connected to a reference probe 15 for projecting the near-infrared light on a reference plate "T" such as a ceramic plate. The optical system is disposed at a light irradiating side between the light source 10 and the first and second optical-fibers (12, 14), and comprises, for example, an optical member 16 having a pin hole, lenses 17, and a beam splitter 18 for dividing the near-infrared light emitted from the light source 10 into the first and second optical fibers (12, 14), respectively.

By the way, the skin of a living body such as human is generally composed of an epidermis layer including a cornified layer, dermis layer, and an underneath hypodermis layer. An appropriate thickness of the epidermis layer is in a range of 0.2 to 0.4 mm. An appropriate thickness of the dermis layer is in a range of 0.5 to 2 mm. An appropriate thickness of the hypodermis layer is in a range of 1 to 3 mm. In the dermis layer, the in-vivo components are easily transferred through capillary blood vessels. In particular, it is believed that a change in glucose concentration in blood (i.e., blood sugar level) speedily appears as a change in glucose concentration in the dermis layer. On the other hand, since the underneath hypodermis layer contains lipid as the main component, the water-soluble in-vivo component such as glucose is hard to uniformly exist in the hypodermis layer. From these considerations, it is desired to selectively measure a near-infrared absorption spectrum from the dermis layer to accurately determine the glucose concentration in blood.

Figure 2:
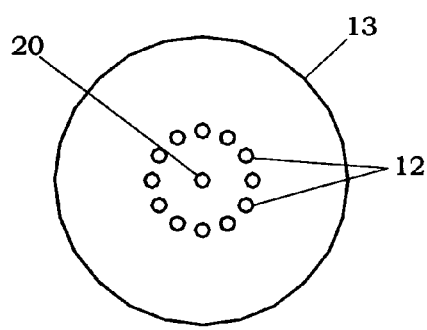
FIG. 2 is an end view of a measurement probe of the apparatus.

In this embodiment, the first optical fibers 12 are arranged at an end surface of the measurement probe 13, as shown in FIG. 2. That is, ends surface of the first optical fibers 12 are evenly spaced from each other on the circumference of a circle having a predetermined radius. In addition, as described later, a third optical fiber 20 for receiving the resultant radiation from the skin is disposed at a center of the circle. It is preferred that the radius of the circle is 2 mm or less. In this embodiment, the radius is 0.65 mm. The reference probe 15 has a substantially same structure as the measurement probe 13.

The light receiving unit comprises the third optical fiber 20 having one end connected to the measurement probe 13, fourth optical fiber 22 having one end connected to the reference probe 15, and a light receiving device 29 optically connected to the other ends of the third and fourth optical fibers (20, 22) through an optional optical system to receive the resultant radiations from the skin "S" or the reference plate "T". The optical system 24 is disposed at a light receiving side between the third and fourth optical fibers (20, 22) and the light receiving device 29, and comprises, for example, a shutter 25, lenses 26, reflection mirror 27 and diffraction grating 28 and so on. Thus, after the near-infrared light is incident on the skin "S" of the subject from the measurement probe 13, and then reflected and/or diffused in the skin, the resultant radiation from the skin is received by the light receiving device 29 through the third optical fiber 20.

In this embodiment, to compensate fluctuations of the near-infrared light caused by a change in ambient temperature, positional relations between optical members and so on, the resultant radiation from the reference plate "T" is used as the reference light. That is, the near-infrared light emitted from the light source 10 is incident on a surface of the reference plate from the reference probe 15, and then the resultant radiation is received by the light receiving device 29 through the fourth optical fiber 22. In this case, by controlling the optical system, one of the resultant radiations provided from the third and fourth optical fibers (20, 22) is selectively received by the light receiving device 29.

The light received by the light receiving device 29 is converted into a corresponding electric signal, and then an A/D conversion is performed by an A/D converter 40. An output of the A/D converter 40 is sent to the operation unit 50 such as a personal computer. In the operation unit 50, a spectrum analysis of the received light is performed to calculate the concentration of the in-vivo component according to the method described later. Specifically, the operation unit 50 calculates the concentration of the in-vivo component by analyzing a minute change in absorption spectrum derived from a change in concentration of the in-vivo component according to a multivariate analysis such as PLS analysis with use of a signal "Ref" obtained from the reference plate "T" and a signal "Sig" obtained from the skin "S" of the subject. The absorption "Abs" is expressed by log 10(Ref/Sig).

Figure 3:
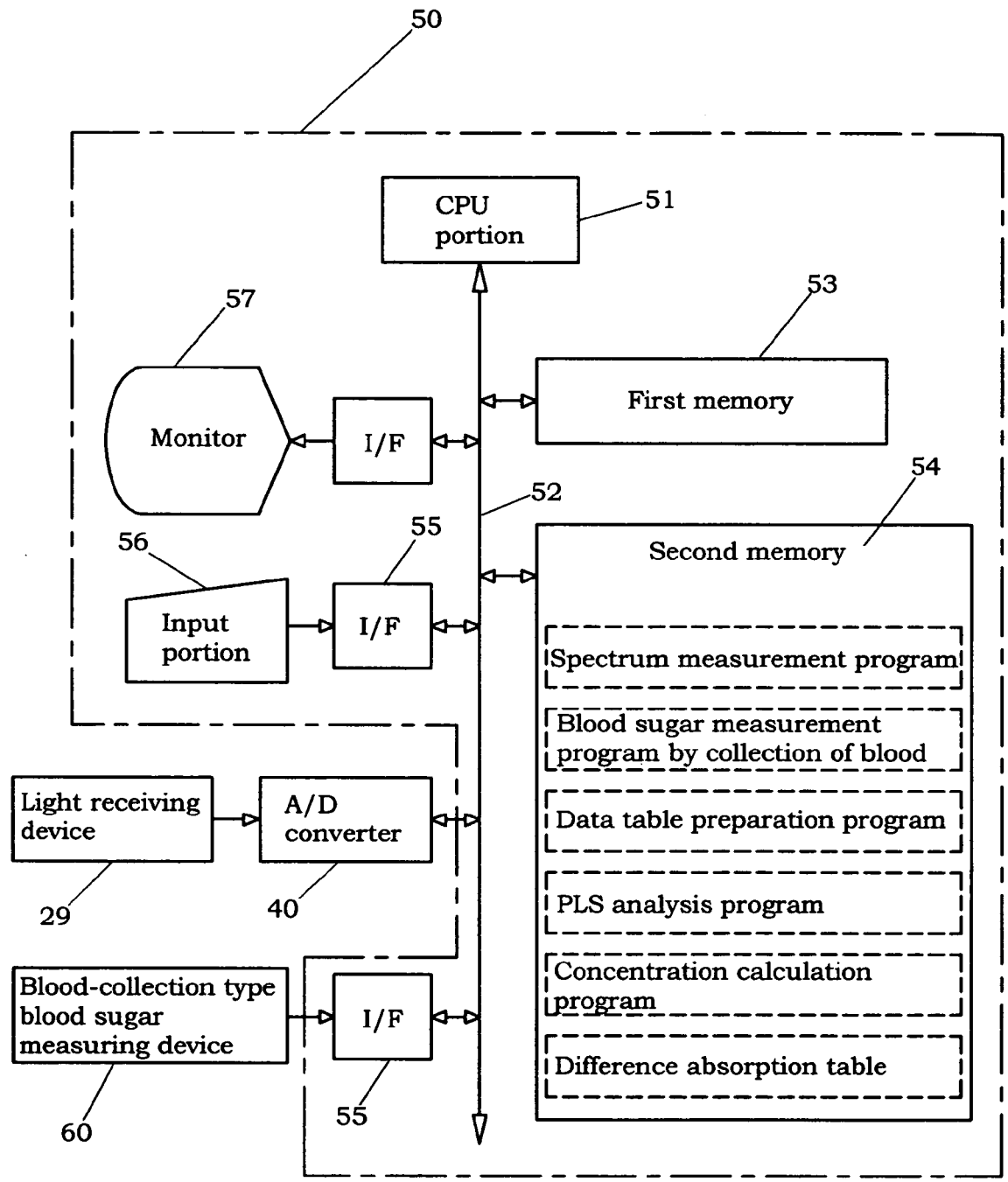
FIG. 3 is a block diagram of an operation unit of the apparatus.

FIG. 3 shows an example of the operation unit 50. This operation unit 50 is basically composed of a CPU portion 51, first memory 53 composed of RAM used to ensure a working area and temporarily store data and ROM used to store a basic program, and second memory 54 such as a fixed disc device for storing required programs and data, which is connected to the first memory 53 and the CPU portion 51 through an internal bus 52. The output of the light receiving device 29 is sent to the internal bus 52 through the A/D converter 40. As described before, a device 60 for measuring the concentration of the in-vivo component (e.g., blood sugar level) by means of collection of blood in order to prepare the calibration curve, is connected to the internal bus 52 through an interface portion 55.

Figure 4:
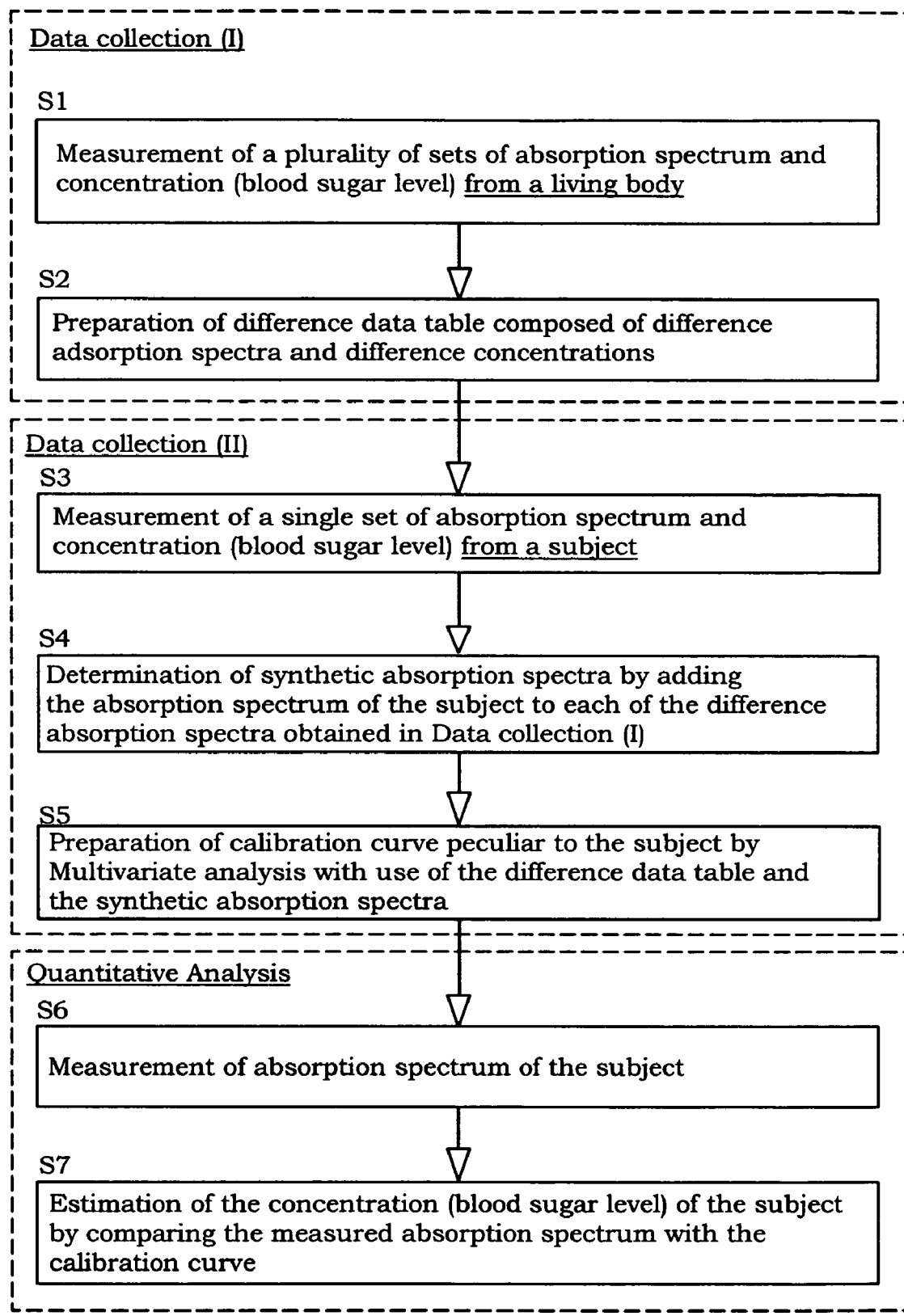
FIG. 4 is a flowchart of a method of preparing a calibration curve of the present invention.

In this embodiment, data needed to prepare the calibration curve is measured from a living body. That is, as shown in FIG. 4, a plurality of sets of absorption spectrum of the living body, and concentration of the target in-vivo component (e.g., blood sugar level in this embodiment) of the living body are measured plural times (S1). In each of the sets, the concentration is measured at a substantially same timing as the measurement of the absorption spectrum. When the calibration curve is prepared for a subject, the living body, from which the data needed to prepare the calibration curve is measured, is not limited to the subject. For example, the living body may be any persons other than the subject. When measuring the blood sugar level, it is preferred to measure the absorption spectrum in a wavelength region of 1200 nm to 1880 nm because the absorption derived from glucose molecule is large and the absorption derived from water molecule is relatively small.

Next, one of the measured absorption spectra is selected as a reference absorption spectrum. In addition, one of the measured concentrations (i.e., blood sugar levels) is selected as a reference concentration. By subtracting the reference absorption spectrum from each of the measured absorption spectra, a plurality of difference absorption spectra are obtained. Similarly, a plurality of difference concentrations are obtained by subtracting the reference concentration from each of the measured concentrations. As a result, a difference data table composed of the difference absorption spectra and the difference concentrations is prepared and stored in the second memory 54 (S2).

The measured concentration used as the reference concentration and the measured absorption spectra used as the reference absorption spectrum are the data obtained at about the same time. In addition, there are needed to satisfy the following conditions.

(1) When the sets of the absorption spectrum and the concentration are measured from a plurality of persons as the living body, the set of the reference spectrum and the reference concentration are determined every person. By satisfying this condition, it is possible to obtain the difference absorption spectrum without including the influence of differences among individuals.

(2) When the sets of the absorption spectrum and the concentration are measured in different days, the reference spectrum and the reference concentration are determined every day. By satisfying this condition, it is possible to obtain the difference absorption spectrum without including the influence of difference among days.

To obtain a higher reliability of the calibration curve, it is preferred to measure the sets of the absorption spectrum and the concentration from the plural persons in the different days.

The data collection described above is explained from the viewpoint of the operation unit 50. In the operation unit 50, the CPU portion 51 carries out a spectrum measurement program stored in the second memory 54 to determine the absorption spectrum from the light signal received by the light receiving device 29. On the other hand, the CPU portion 51 also carries out a blood sugar measurement program stored in the second memory 54. Data obtained by the device 60 of measuring the blood sugar level by means of collection of blood is sent to the internal bus 52 through the interface portion 55 to determine the concentration (blood sugar level). Then, the CPU portion 51 carries out a data table preparation program stored in the second memory 54, so that the difference absorption spectra and the difference concentrations are determined to prepare the difference data table. The thus obtained difference data table is stored in the second memory 54.

Figure 5A:
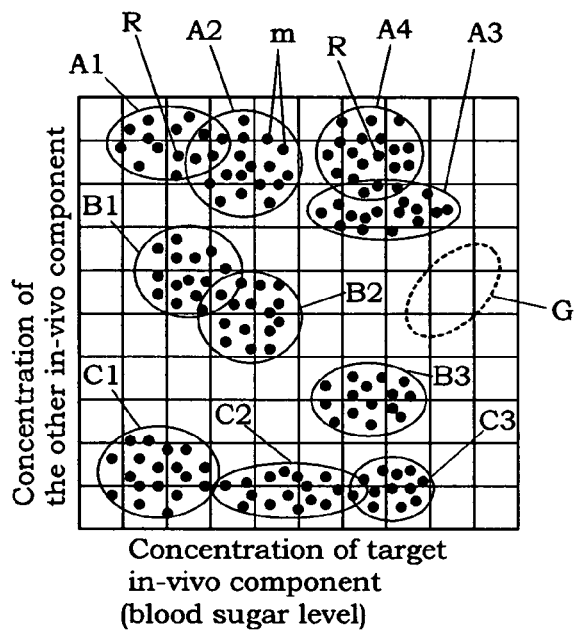
FIGS. 5A to 5C shows data for preparing the calibration curve of glucose (blood sugar level)
Figure 5B:
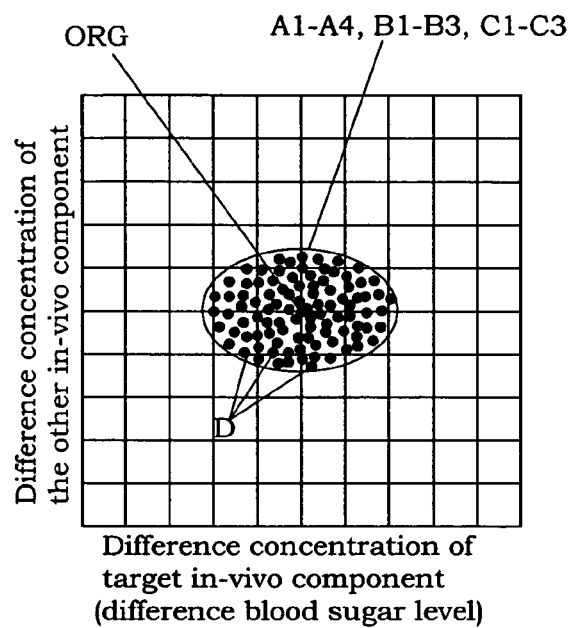

The importance of using difference values in the present invention is briefly explained below. In a conventional method, as described before, it is difficult to obtain high estimation accuracy at the data poor region G by the calibration curve prepared from the measurement results of FIG. 5A. To ensure a stable reliability of the estimation accuracy, it is needed to measure considerably large amounts of data for preparation of the calibration curve. On the other hand, when a reference value "R" is determined from the measurement values "m" in each of the ellipses (A1~A4, B1~B3, C1~C3) in FIG. 5A, and difference values "D" are determined by subtracting the reference value "R" from each of the measurement values "m", the difference values "D" are gathered in a narrow region around an origin point "ORG", as shown in FIG. 5B. Even when a concentration value to be estimated is in the poor dotted region "G" in FIG. 5A, the data in such a region can be relocated around the origin point "ORG" by determining the difference values. Therefore, by using the difference data, it is possible to obtain the calibration curve with a stable estimation accuracy, which does not include the influences of difference among individuals and differences among days, without measuring the considerably large amounts of data.

Next, a single set of the absorption spectrum and the concentration value of the target in-vivo component of the subject, which needs the quantitative analysis of the target in-vivo component (e.g., blood sugar level), is determined according to a similar manner to the above, as shown by (S3) in FIG. 4. The measured absorption spectrum of the subject is defined as a second reference absorption spectrum. Similarly, the measured concentration value of the subject is defined as a second reference concentration. When a plurality of absorption spectra are measured from the subject, an average thereof can be used as the second reference absorption spectrum. Similarly, when a plurality of concentration values are measured from the subject, an average thereof can be used as the second reference concentration. In this case, it is based on condition that the measured concentrations have an approximately same value. In addition, it is not needed that the concentration value used as the second reference concentration and the adsorption spectrum used as second reference absorption spectrum are the data obtained at about the same time.

Next, each of the difference absorption spectra is synthesized with the second reference absorption spectra to obtain a plurality of synthetic absorption spectra (S4). The thus obtained synthetic absorption spectra provide absorption spectra peculiar to the subject corresponding to the concentration fluctuations within one day of the target in-vivo component.

Next, as shown by (S5) in FIG. 4, a multivariate analysis such as PLS analysis is performed with use of the synthetic absorption spectra and the difference data table to prepare the calibration curve, which is often called as calibration function. By use of this calibration curve, a concentration value of the target in-vivo component of the subject can be estimated from the near-infrared absorption spectra non-invasively measured from the subject. In the present invention, since the difference data table composed of the difference absorption spectra and the difference concentrations are previously prepared, the calibration curve peculiar to the subject can be speedily obtained by measuring only a single pair of the absorption spectrum and the concentration value of the target in-vivo component from the subject. The thus obtained calibration curve includes the information peculiar to the subject and the information about fluctuations within one day of other factors, and for example, the number of principal components is approximately in a range of 7 to 10.

The preparation of the calibration curve described above is explained along the flow chart of FIG. 6. When an order of preparing the calibration curve is input in the operation unit 50 through an input portion unit 56 (S10), the CPU portion 51 carries out the spectrum measurement program to measure the second reference absorption spectrum of the subject (S11). In addition, the CPU portion 51 also carries out the blood sugar measurement program, so that the second reference concentration (blood sugar level) of the subject is determined from the data measured by the device 60 of measuring the blood sugar level by means of collection of blood (S12). Subsequently, the second reference absorption spectrum is synthesized with each of the difference absorption spectra to obtain the synthetic absorption spectra (S13). It is not needed to synthesize the second reference concentration with each of the difference concentrations. The second reference concentration can be used as a bias value at the time of determining a concentration value of the target in-vivo component of the subject.

Figure 7:
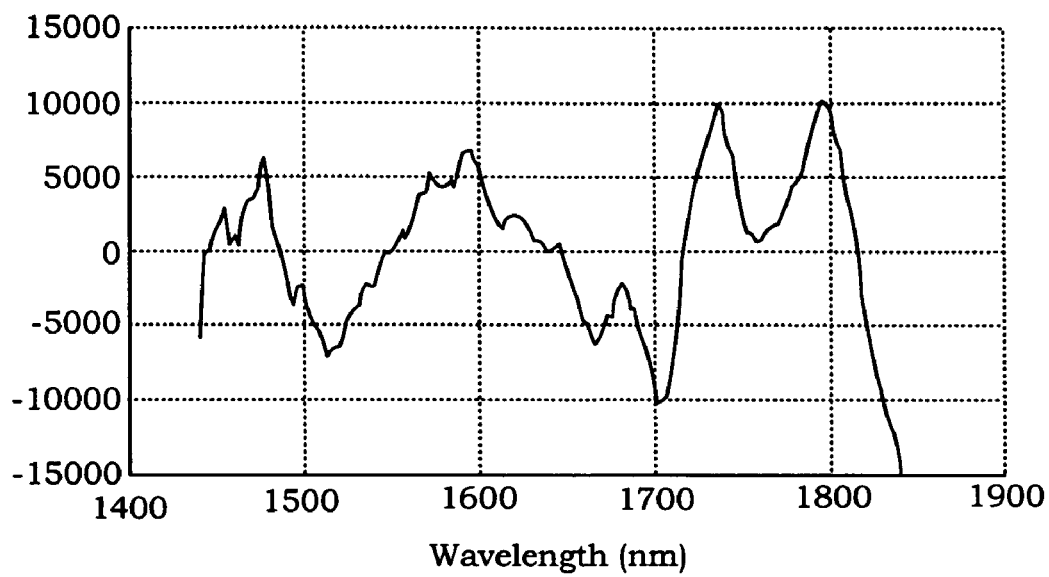
FIG. 7 is a calibration curve prepared by the method of the first embodiment.

Next, the CPU portion 51 carries out a PLS analysis program stored in the second memory 54 to prepare the calibration curve by use of the synthetic absorption spectra and the difference data table stored in the second memory 54 (S14). The thus obtained calibration curve is stored in the second memory 54 (S15). As an example, a calibration curve obtained by the above procedures is shown in FIG. 7. It is understood from this figure that the calibration curve has an absorption peak of glucose as the target in-vivo component at about 1600 nm. As described later, a similar calibration curve can be obtained by the method of the second embodiment using a light propagation simulation.

By use of the obtained calibration curve, the concentration of the target in-vivo component is non-invasively measured. That is, the near-infrared light is irradiated to the skin of the subject to measure a near-infrared absorption spectrum (S6). The concentration value of the target in-vivo component of the subject at the time of measuring the absorption spectrum can be estimated by comparing the measured absorption spectrum with the calibration curve (S7).

Figure 6:
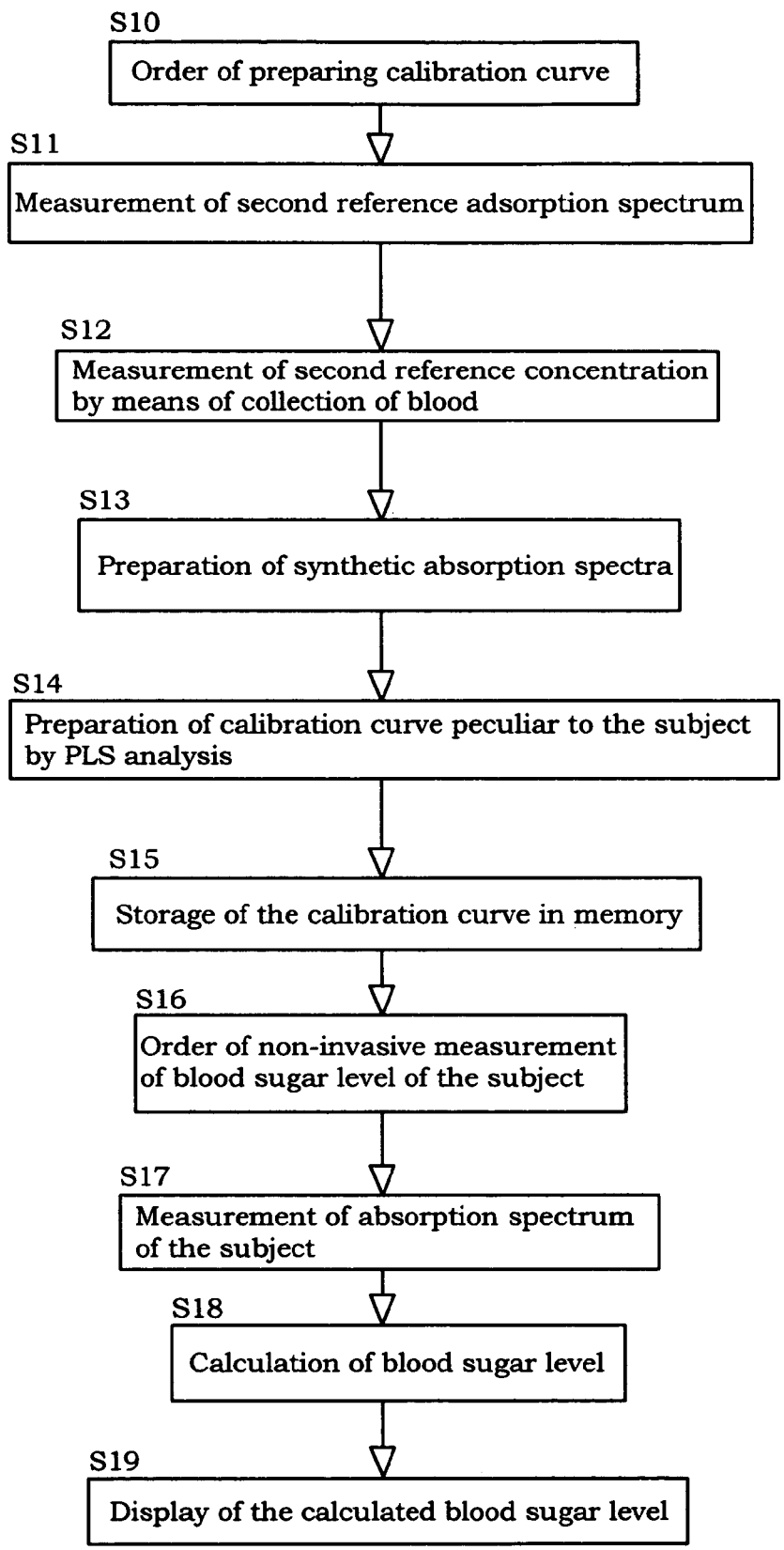
FIG. 6 is a detailed flowchart of the method of preparing the calibration curve.

The quantitative analysis of the target in-vivo component of the subject is explained along the flow chart of FIG. 6. When an order of the quantitative analysis is input in the operation unit 50 though the input portion 56 (S16), the CPU portion 51 carries out the spectrum measurement program to measure the absorption spectrum of the subject (S17). After the measurement is finished, the CPU portion 51 carries out a concentration (blood sugar) calculation program. That is, the CPU portion 51 reads out the calibration curve peculiar to the subject stored in the second memory 54, and compare the measured absorption spectrum with the calibration curve to calculate the concentration value of the target in-vivo component of the subject (S18). The calculated concentration value is displayed on a monitor 57 through the interface portion (S19). Thus, since the calibration curve with a stable reliability in estimation accuracy is obtained by the method of the present invention, it is possible to successively measure the concentration value of the target in-vivo component of the subject in a non-invasive manner.

In the above method, the target in-vivo component is not limited to glucose. For example, other components such as protein, lipid, water and urea may be the target in-vivo component. In this case, it is needed to store programs adequate for a desired target in-vivo component in the second memory 54.

Second Embodiment

A method of preparing a calibration curve of this embodiment is substantially the same as the method of the first embodiment except that the difference absorption spectra are obtained according to a light propagation simulation, which is defined as a method of analyzing a light propagation in a simulated living body. Therefore, duplicate explanations are omitted. In addition, an apparatus with the same configuration as the first embodiment can be used to perform the quantitative analysis in this embodiment.

In this embodiment, a Monte Carlo simulation is used as the light propagation simulation. The Monte Carlo simulation is known as a statistical method for accurately recreating an objective phenomena by use of a function based on the occurrence probability distribution of the objective phenomena with respect to uniform random numbers generated in a region of 0 to 1 by a calculator.

In the case of recreating the light propagation, a light incident on a medium is regarded as a bunch of photons. The behavior of each of the photons in the medium is tracked according to optical characteristics of the medium ("$\mu_a$" absorption coefficient, "$\mu_s$": scattering coefficient, "p ($\theta$)": scattering phase function, "n": refraction index). As a result, the light propagation in the medium can be statistically recreated from the behaviors of all of the photons. "$\theta$" of the scattering phase function is an angular change of the traveling direction of light caused by a single scattering on the assumption of symmetry with respect to azimuthal angle. An effective description of the scattering phase function is represented by a Henyey-Greenstein function, as shown by the following equation (1), which is often used to express a scattering phenomena in a living body including red blood cells.

$$p(\Theta) = \frac{1-g^2}{(1+g^2-2g\cos\Theta)^{3/2}} \quad (1)$$

In the above equation (1), "g" is a anisotropic scattering parameter, by which the anisotropic property of scattering expressed by "p (θ)" can be more simply characterized. The parameter "g" is in a range of −1 to 1. When the parameter "g" is 1, 0 or −1, the scattering property is correspondingly expressed by a perfect forward scattering, isotropic scattering or a backward scattering. For example, the scattering property in the living body is expressed by a very strong forward scattering. In addition, the scattering property in a medium having poor absorption can be approximately expressed by the isotropic scattering.

In addition, according to the above approximation, the scattering coefficient "$\mu_s$" is provided by a reduced scattering coefficient "$(1-g)\mu_s$". A light path length "L" between two successive interactions (absorption, scattering) in the light propagation is represented by the following equation (2). In addition, changes (Θ, φ) of the zenith angle and the azimuthal angle of refraction at the interactions are respectively represented by the following equations (3) and (4).

$$L = -\frac{\ln(r_1)}{\mu_a + \mu_s} \quad (2)$$

$$\Theta = \int^{-1} (R_2) \quad (3)$$

$$\phi = 2\pi R_3 \quad (4)$$

In the above equations, each of "R1", "R2" and "R3" is a uniform random number in a range of 0 to 1, and "$f(\theta)$" is a cumulative probability of the scattering phase function. In addition, an energy of the photon at the first interaction is absorbed according to the absorption property of the medium, which is represented by the following equation (5).

$$W_{i+1} = \left(\frac{\mu_s}{\mu_a + \mu_s}\right) \quad (5)$$

By the way, the skin of the living body comprises a horny layer, granular layer, stratum spinosum, and a basal layer. The basal layer is composed of a single layer of basal cells, and fresh cells are constantly generated by cell division. The fresh cells are upwardly moved toward the skin surface, so that they change in order of prickle cells→granule cells→horny cells. As a result, the horny layer is formed. In the case of normal horny cells, a single layer of the horny cells fall off every day. A time period between the birth of the basal cells and the generation of the horny cells is approximately two weeks. A time period between an appearance of the fresh horny cells on the skin surface and the falling off thereof is approximately two weeks. Therefore, the epidermis layer is generally born again every four weeks. This means that the epidermis layer is composed of more than 20 cell layers. In the dermis layer, there are glandulae sudoriferae, hair glands, and hair roots in addition to blood vessels, lymph vessels and nerves. Due to active physiological actions in the dermis layer, nutritions are supplied from the blood, and used to generate the fresh cells in the basal layer. In addition, the dermis layer has a fibrous structure, which provides resiliency of skin, while holding the skin. It is believed that the hypodermis layer is mainly formed by subcutaneous lipid. Therefore, it can be considered that glucose is mainly distributed in the dermis layer, and the presence of glucose in the epidermis layer and the hypodermis layer is almost negligible.

Figure 8:
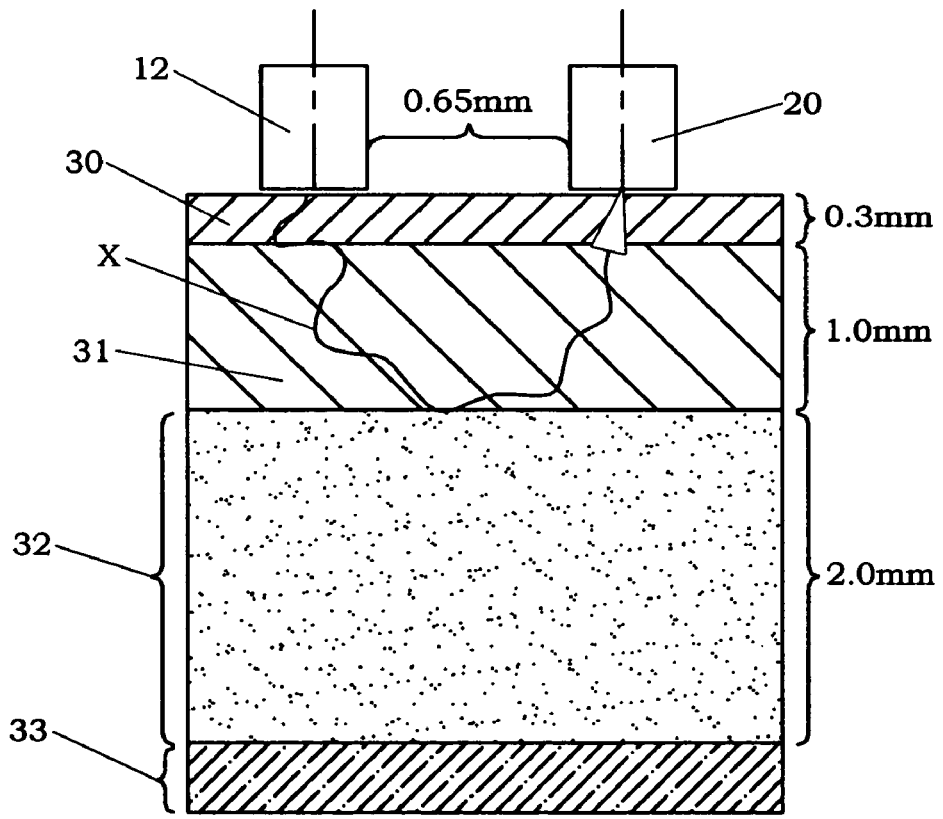
FIG. 8 is a cross sectional view of a simulated tissue of human's skin.

FIG. 8 shows a simulation model of the skin. In this figure, the numerals 30, 31, 32, 33 respectively designates the epidermis layer, dermis layer, hypodermis layer and muscles or bones. For example, the near infrared light irradiated to the skin from the first optical fiber 12 is propagated along a path "X" shown in FIG. 8 in the skin, and then received by the third optical fiber 20.

Figure 9:
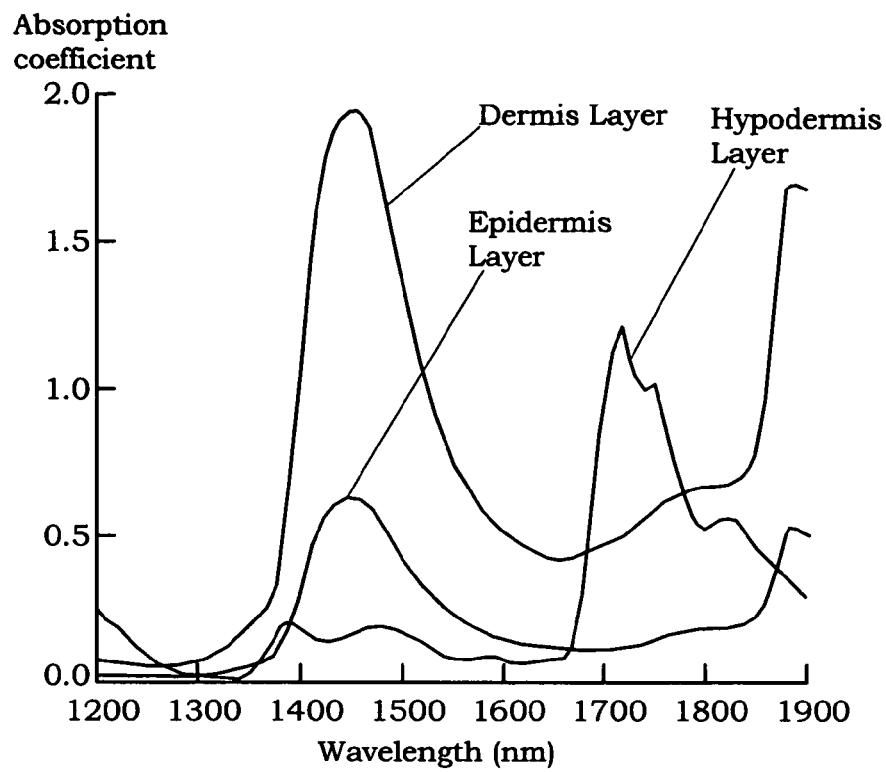
FIG. 9 is a graph showing relationships between wavelength and absorption coefficient at different layers of human's skin.
Figure 10:
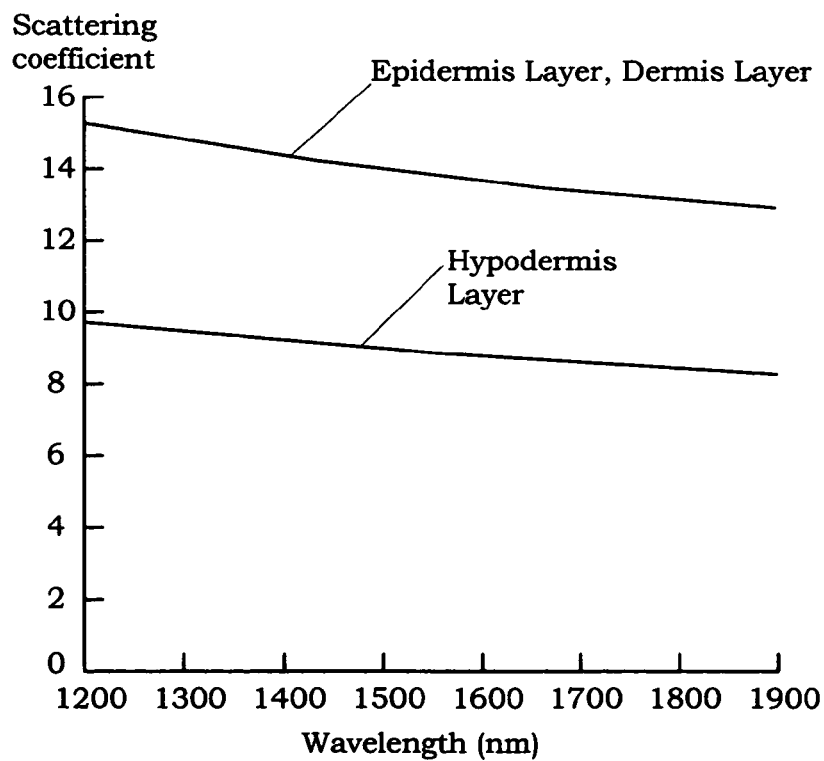
FIG. 10 is a graph showing relationships between wavelength and scattering coefficient at the different layers of human's skin.
Figure 11:
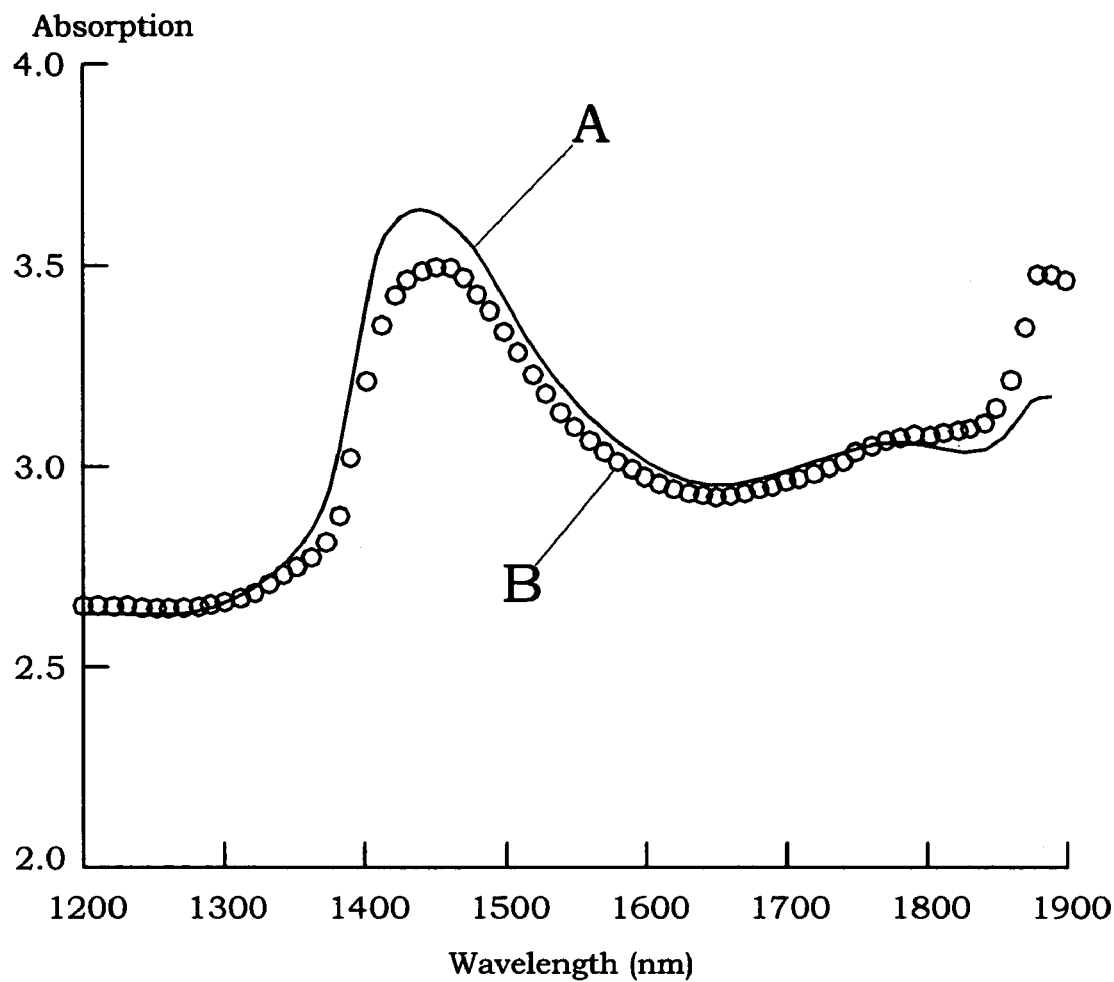
FIG. 11 is a graph showing a comparison between a measured absorption spectrum and a simulated absorption spectrum.

In the case of performing the light propagation simulation according to the Monte Carlo simulation, it is needed to determine the optical characteristics described above, i.e., absorption coefficient "$\mu_a$", scattering coefficient "$\mu_s$", refraction index "n", and anisotropic scattering parameter "g" of each of the epidermis layer, dermis layer and the hypodermis layer. FIG. 9 shows the absorption coefficients "$\mu_a$" of these layers. In addition, FIG. 10 shows the scattering coefficients "$\mu_s$" of these layers. In general, "g" of the living body is provided by a very strong forward scattering of 0.8 to 0.95. Therefore, "g" used in this embodiment is 0.9 constant. In addition, the refraction indexes "n" of these layers is 1.34 constant. FIG. 11 shows a measured absorption spectrum (A) and a simulated absorption spectrum (B) according to the Monte Carlo simulation under the above-described conditions. The preparation of the simulated absorption spectrum is repeated by changing the in-vivo parameters (optical characteristics) such as concentrations of glucose, protein, lipid and water as well as temperature over a predetermined range to cover the fluctuation within one day of each of the in-vivo parameters. Thus, since a plurality of simulated absorption spectra are obtained, the difference absorption spectra are determined according to the same procedures as the first embodiment. As a result, it is possible to obtain a difference data table by the simulation in place of measuring the data from the living body.

Figure 5C:
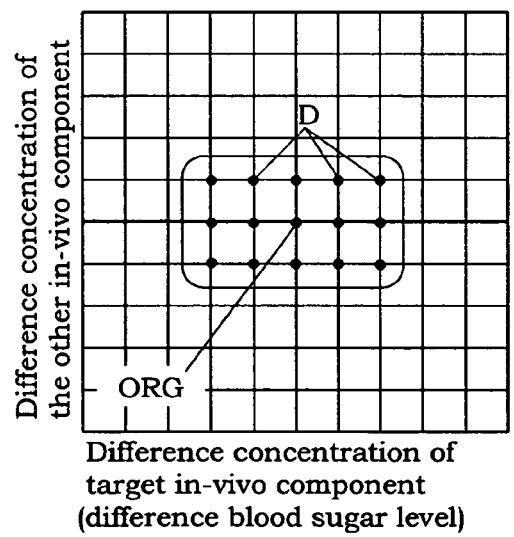
Figure 12:
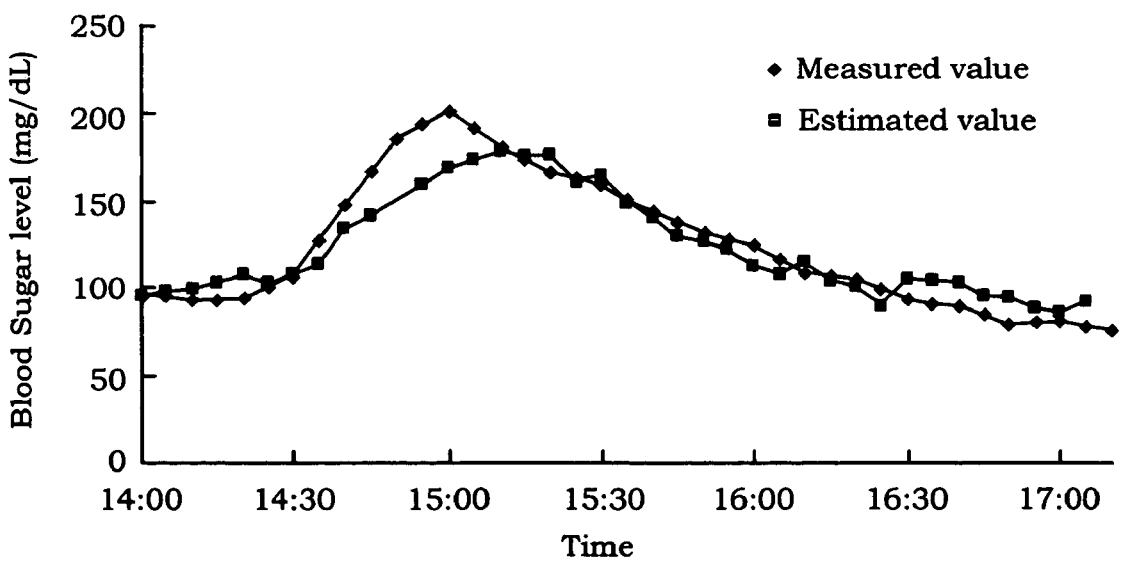
FIG. 12 is a graph showing a comparison between measured blood sugar levels and estimated blood sugar levels of a subject.

Advantages of using the simulation in the present invention are briefly explained below. In the simulation, a fluctuation range within one day of the concentration of the target in-vivo component such as glucose can be predetermined, and then difference values "D" are simulated at equally spaced points around the origin point "ORG" in the fluctuation range, as shown in FIG. 5C. In the case of measuring the data required for the preparation of the calibration curve from the living body, it is difficult to obtain equally spaced difference values "D" within a short time period, as shown in FIG. 5B. However, according to the simulation, it is possible to speedily obtain the difference values, which are suitable to prepare the calibration curve having a stable reliability in estimation accuracy without collecting the large amounts of data. In addition, it is very difficult to determine as to whether the actually measured data contains a weak signal of glucose. However, according to the simulation, it is possible to certainly recreate such a weak signal of glucose. Furthermore, according to the simulation, it is possible to prevent the occurrence of an error between devices for measuring the absorption spectra from the living body and the influence of noise components generated during the measurement on the weak signal of glucose. Therefore, there is no accidental correlation in the simulation. As an example, FIG. 12 shows changes of measured blood sugar level and estimated blood sugar level by using the calibration curve prepared in this embodiment of a subject with respect to time. In this case, a correlation coefficient (r) therebetween is 0.94.

Next, a plurality of synthetic absorption spectra are determined from the difference absorption spectra obtained by the simulation, and a second reference absorption spectrum measured from a subject, as in the case of the first embodiment. The thus obtained synthetic absorption spectra contain information peculiar to the subject. The calibration curve of the second embodiment is obtained by performing a multivariate analysis with use of the synthetic absorption spectra and the difference data table.

Third Embodiment

A method of preparing a calibration curve of this embodiment is substantially the same as the method of the first embodiment except that the near-infrared absorption spectra used to prepare the calibration curve are measured from an imitation sample in place of the living body. Therefore, duplicate explanations are omitted. In addition, an apparatus with the same configuration as the first embodiment can be used to perform the quantitative analysis in this embodiment.

In this embodiment, a suspension containing a light scattering material such as lipid emulsion preparations (for example, "Intralipid" manufactured by Fresenius Kabi Japan) was used as the imitation sample. In particular, a solution containing 2 to 5% of the lipid emulsion preparation "Intralipid" is close to the living body. A plurality kinds of test solutions are prepared by changing a mixture ratio of an in-vivo component such as glucose, protein, lipid, and water relative to the lipid emulsion preparation or changing the solution temperature over a predetermined range to cover fluctuations within one day thereof. With respect to each of the test solutions, the absorption spectrum is measured. One of the measured absorption spectra is selected as the reference absorption spectrum. Since a plurality of difference absorption spectra are obtained by subtracting the reference absorption spectrum from each of the measured absorption spectra, as in the case of the first embodiment, and the concentration value of the in-vivo component in the respective test solution is accurately given, it is possible to prepare a difference data table according to the data measured from the imitation sample in place of the living body.

Next, a plurality of synthetic absorption spectra are determined from the difference absorption spectra obtained by use of the imitation sample, and a second reference absorption spectrum measured from a subject, as in the case of the first embodiment. The thus obtained synthetic absorption spectra contain information peculiar to the subject. The calibration curve of the third embodiment is obtained by performing a multivariate analysis with use of the synthetic absorption spectra and the difference data table.

Fourth Embodiment

A method of preparing a calibration curve of this embodiment is characterized in that the absorption spectra of the target in-vivo component (e.g., glucose) are determined by use of the simulation described in the second embodiment, and with respect to the other in-vivo parameter (e.g., protein, lipid, water, scattering or temperature), the absorption spectra are actually measured from a living body on the condition that the concentration of the target in-vivo component is constant according to the similar procedures to the first embodiment. Therefore, duplicate explanations are omitted. In addition, an apparatus with the same configuration as the first embodiment can be used to perform the quantitative analysis in this embodiment.

For example, in the case of preparing the calibration curve of glucose by the multivariate analysis, it is preferred to consider the absorption spectra of the in-vivo component other than glucose. In the living body, when the glucose concentration changes, a change in concentration of the other in-vivo component simultaneously occur. Therefore, the absorption spectra of the other in-vivo parameters are useful to remove the influence of the other in-vivo component from the calibration curve of glucose. On the other hand, the weak signal of glucose can be certainly recreated by using the simulation, as described in the second embodiment. Therefore, according to this embodiment, it is possible to provide the calibration curve with a further improvement in estimation accuracy.

In addition, when measuring the absorption spectra from the living body with respect to the other in-vivo component, the living body is not limited to the subject, which needs the quantitative analysis. For example, the living body may be at least one of persons other than the subject. One of the measured absorption spectra is selected as a reference absorption spectra, and a plurality of difference absorption spectra are determined, as in the case of the first embodiment. At this time, since the concentration of the target in-vivo component is kept constant, it is not needed to determine the difference concentrations.

In this embodiment, a difference data table is prepared from the difference absorption spectra determined from the measurement data with respect to the other in-vivo component, the difference absorption spectra determined by the simulation with respect to the target in-vivo component, and the difference concentrations of the target in-vivo component. Next, a plurality of synthetic absorption spectra are determined by synthesizing each of the difference absorption spectra determined by the simulation with a second reference absorption spectrum measured from the subject, as in the case of the second embodiment. The thus obtained synthetic absorption spectra contain information peculiar to the subject. The calibration curve of the fourth embodiment is obtained by performing the multivariate analysis with use of the synthetic absorption spectra and the difference data table.

According to the present embodiment, since the calibration curve is prepared in consideration of the influence of the other in-vivo component(s), which can not be considered by the simulation, it is possible to achieve a further improvement in estimation accuracy of the concentration of the target in-vivo component, while ensuring the advantages of the second embodiment brought by using the simulation such as the effects of reducing noise components, and improving the stability of the estimation accuracy.

In the first to fourth embodiments described above, it is preferred to measure absorption spectra under at least two different conditions in an expected range of fluctuations within one day of the absorption spectrum with respect to an in-vivo parameter other than the target in-vivo component (e.g., glucose). For example, when the other in-vivo parameter is temperature, two temperatures of a reference temperature $\pm 1°$ C. can be selected. In addition, when the other in-vivo parameter is protein concentration, two protein concentrations of a reference concentration $\pm 10\%$ can be used. In this case, the difference absorption spectra change in response to a value of the reference concentration. However, when the glucose concentration is a criterion variable, the concentration values of the other in-vivo component are not needed in the multivariate analysis. Thus, if necessary, the calibration curve may be prepared in consideration of the fluctuations of the other in-vivo parameters such as temperature and protein concentration.

Fifth Embodiment

In the first embodiment, the multivariate analysis with use of the synthetic absorption spectra is performed to prepare the calibration curve. This embodiment is characterized in that the calibration curve is prepared by the multivariate analysis with use of difference absorption spectra. Therefore, the calibration curve of this embodiment provides a difference concentration of the target in-vivo component (e.g., glucose). Other configurations are substantially the same as the embodiments described above except for the following explanation. Therefore, duplicate explanations are omitted. In addition, an apparatus with the same configuration as the first embodiment can be used to perform the quantitative analysis in this embodiment.

In this embodiment, a measurement of an absorption spectrum from a living body is repeated plural times in a plurality wavelength regions defined in a near-infrared region of 1000 nm to 1880 nm, as shown by "S30" in FIG. 13. For example, the absorption spectrum is measured plural times in a first wavelength region of 1200 nm to 1880 nm, which is a region having a large absorption derived from glucose molecule and a relatively small absorption derived from water molecule, as shown in FIG. 14, and also the absorption spectrum is measured in a second wavelength region of 1000 nm to 1350 nm, which is a region having a relatively small absorption peculiar to water molecule and hemoglobin. The measurements in the first and second wavelength regions are preferably performed at about the same time. In addition, blood sugar levels are simultaneously measured from the living body by means of collection of blood.

Next, a baseline compensation of the absorption spectrum obtained at the first wavelength region is performed (S31) by use of the absorption spectrum obtained at the second wavelength region. In the second wavelength region, the absorptions of water, protein, lipid and hemoglobin are negligibly small. Therefore, profiles of the absorption spectra measured in the second wavelength region are substantially equal to each other in a theoretical sense. However, in fact, a change in scattering phenomena happens due to a change of the background structure. By this influence, positions of the absorption spectra are shifted up and down. Therefore, by performing the baseline compensation with use of the absorption spectra measured in the second wavelength region, it is possible to reduce the influence of the change in scattering phenomena from the absorption spectra measured in the first wavelength region. In this case, the baseline compensation may be performed by estimating a bias value at one wavelength in the second wavelength region. Preferably, when the baseline compensation is performed by estimating bias values at several wavelengths in the second wavelength region and using an average of the bias values, it is possible to further minimize the occurrence of a measurement error of the absorption spectra and the influence of noise components generated during the measurement.

Next, one of the baseline-compensated absorption spectra in the first wavelength region is selected as a reference absorption spectrum (S32), and a plurality of difference absorption spectra are determined by subtracting the reference absorption spectrum from each of the baseline-compensated absorption spectra (S33). When the measurement of absorption spectra is performed over plural days, the reference absorption spectrum is selected every day. In addition, the blood sugar level is measured by means of a collection of blood at a substantially same timing as the respective measurement of the absorption spectrum. Therefore, the calibration curve of this embodiment can be obtained by performing the multivariate analysis with use of the difference absorption spectra and the measured blood sugar levels (S34).

In addition, the measurement of the absorption spectra in the first wavelength region are repeated plural times after the elapse of a required time period. One of the measured absorption spectra is selected as the reference absorption spectrum, and a plurality of difference absorption spectra are determined. By comparing the obtained difference absorption spectra with the calibration curve, it is possible to consider a change in absorption spectrum caused by fluctuations among days of the in-vivo components and a change of the background structure, and therefore obtain the calibration curve having the capability of more accurately performing the quantitative analysis of blood sugar level. In addition, an average of the absorption spectra measured plural times may be used as the reference absorption spectrum. In this case, it is possible to reduce the influences of noise components generated during the measurement and measurement errors, and achieve a further improvement of the estimation accuracy.

FIGS. 15A to 15F are absorption spectra measured plural times at the first wavelength region in each of measurement days (1) to (6). From each of FIGS. 15A to 15F, it can be understood that the profile positions of the absorption spectra are shifted up and down within one day. Each of FIGS. 16A to 16F shows changes with respect to time of measured blood sugar levels and estimated blood sugar levels by the calibration curve, which is prepared by the multivariate analysis with use of the absorption spectra of FIGS. 15A to 15F and the blood sugar levels measured by the collection of blood without determining the difference absorption spectra. These results show that the correlations between the measured blood sugar levels and the estimated blood sugar levels are not very high.

On the other hand, FIGS. 17A to 17F show difference absorption spectra determined after performing the baseline compensation to the absorption spectra shown in FIGS. 15A to 15F. In addition, each of FIGS. 18A to 18F shows changes with respect to time of measured blood sugar levels and estimated blood sugar levels by the calibration curve, which is prepared by the multivariate analysis with use of the difference absorption spectra of FIGS. 17A to 17F and the blood sugar levels measured by the collection of blood. These results show that the correlations between the measured blood sugar levels and the estimated blood sugar levels are remarkably improved, as compared with the results of FIGS. 16A to 16F.

By the way, the baseline compensation may be omitted in this embodiment, if necessary. FIGS. 19A to 19F show difference absorption spectra determined without performing the baseline compensation to the absorption spectra shown in FIGS. 15A to 15F. In addition, each of FIGS. 20A to 20F shows changes with respect to time of measured blood sugar levels and estimated blood sugar levels by the calibration curve, which is prepared by the multivariate analysis with use of the difference absorption spectra of FIGS. 19A to 19F and the blood sugar levels measured by the collection of blood. These results show higher correlations between the measured blood sugar levels and the estimated blood sugar levels, as compared with the results of FIGS. 16A to 16F. However, since the baseline compensation was not performed, the correlations therebetween are not higher than the results of FIGS. 18A to 18F.

Figure 16A:
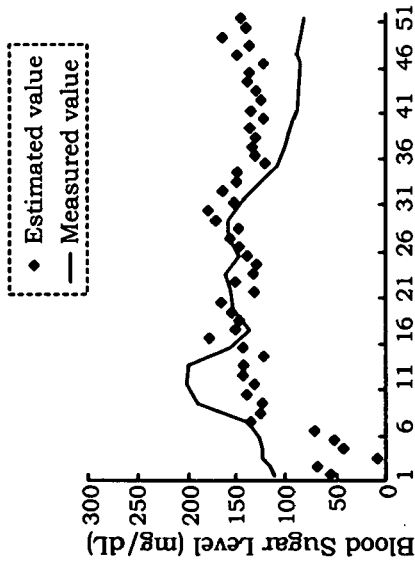
FIGS. 16A to 16F are respectively graphs showing comparisons between measured blood sugar levels and blood sugar levels estimated by use of the data of FIGS. 15A to 15F without determining difference absorption spectra.
Figure 16B:
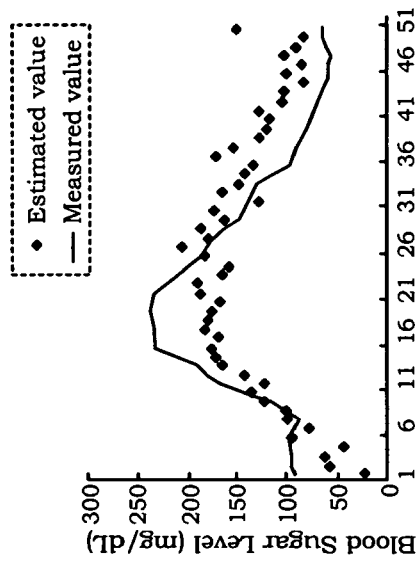
Figure 16C:
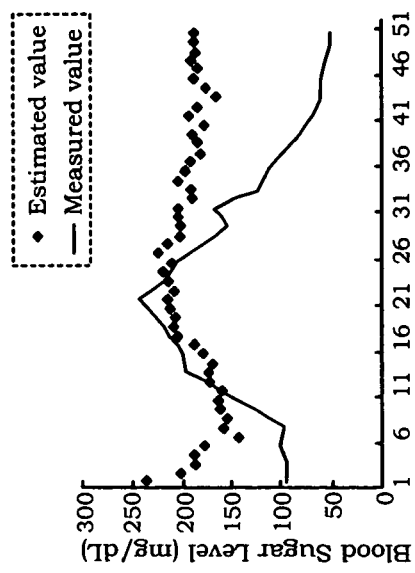
Figure 16D:
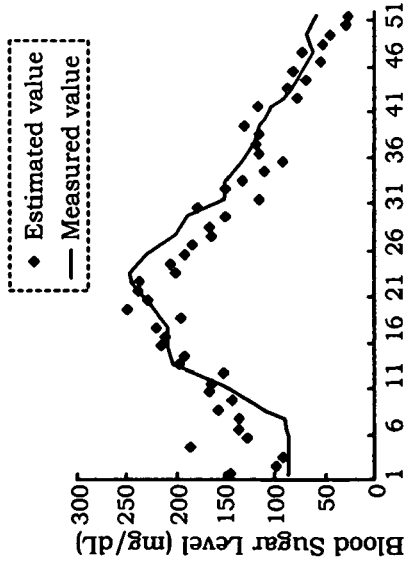
Figure 16E:
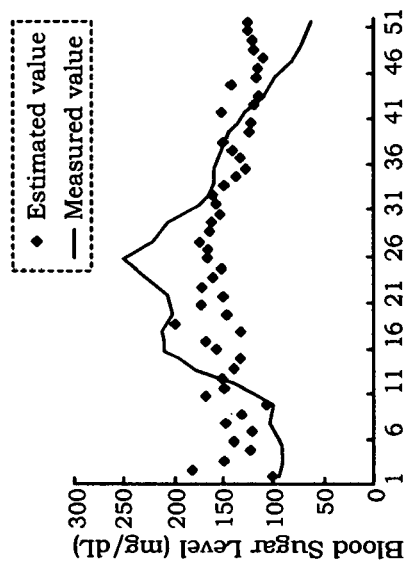
Figure 16F:
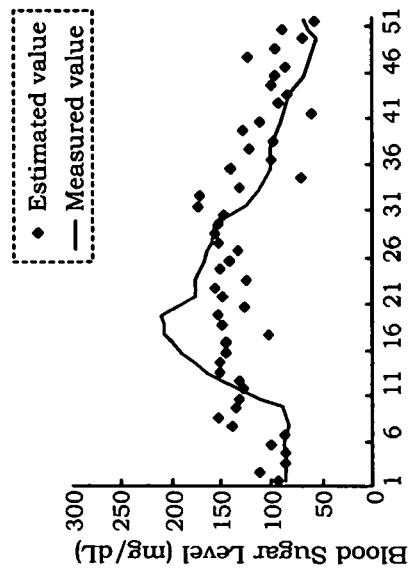
Figure 18A:
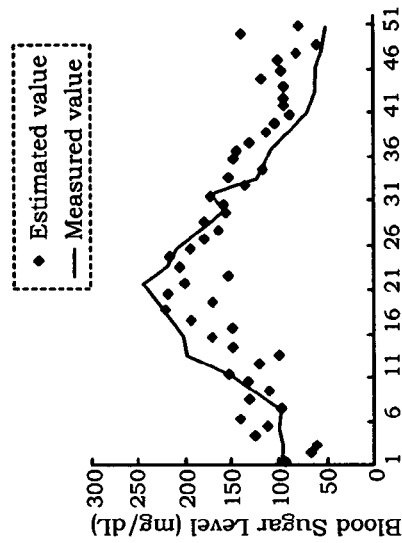
FIGS. 18A to 18F are respectively graphs showing comparisons between measured blood sugar levels and blood sugar levels estimated by use of the data of FIGS. 17A to 17F.
Figure 18B:
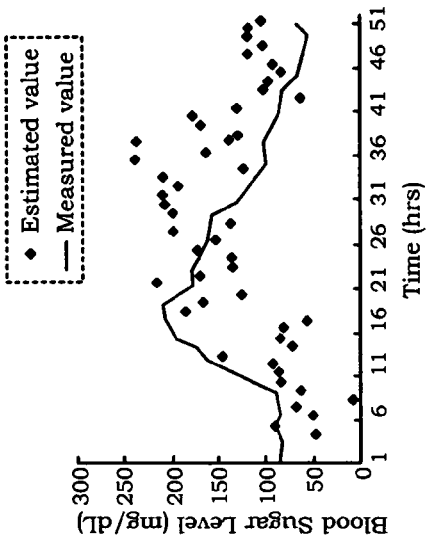
Figure 18C:
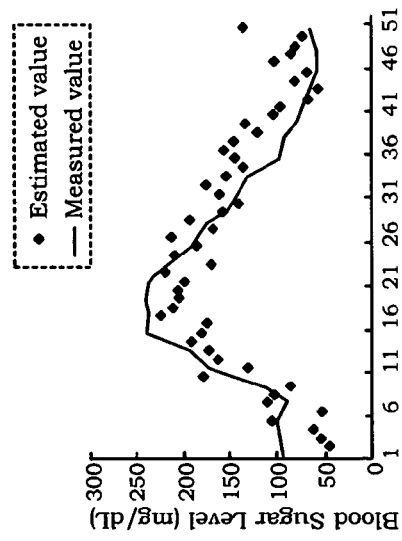
Figure 18D:
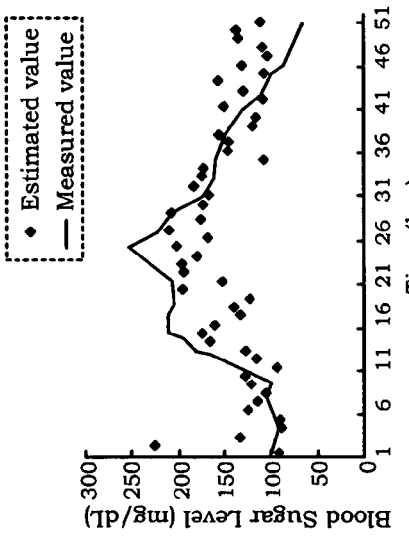
Figure 18E:
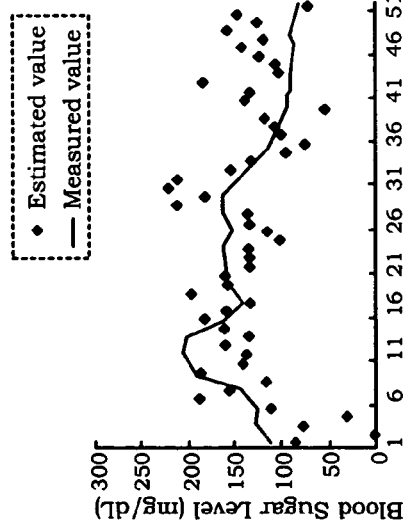
Figure 18F:
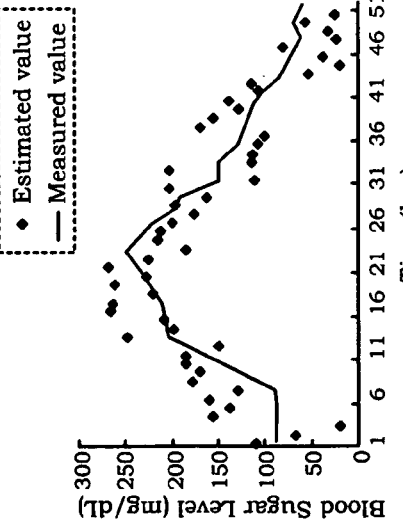

In addition, when comparing the result of FIG. 20F or FIG. 18F with the result of FIG. 16F, the result of FIG. 16F shows a higher correlation. This is believed that there was a problem in the measurement of the absorption spectra. To improve the estimation accuracy, such bad data can be cancelled according to the following method. That is, after the difference absorption spectra are determined, the waveform of each of the difference absorption spectra is checked. For example, when the absorption spectrum corresponding to a low blood sugar level is used as the reference absorption spectrum, the difference absorption spectra having a negative waveform can be regarded as the bad data. Alternatively, when a sum of absorptions at predetermined wavelengths in the difference absorption spectrum is calculated, and then compared with a threshold value, the difference absorption spectrum having the sum smaller than the threshold value can be regard as the bad data.

As a modification of this embodiment, the influence of a change in scattering at the background structure can be removed by the following method. That is, when the absorption spectrum is measured plural times in the first wavelength region of 1200 nm to 1880 nm having a large absorption derived from glucose molecule and a relatively small absorption derived from water molecule, at least one of the measured absorption spectra, preferably the absorption spectrum measured at the time of an empty stomach, i.e., under relatively small fluctuations in blood sugar level, is used as the reference absorption spectrum. For example, the reference absorption spectrum is preferably measured at the blood sugar level of about 100 mg/dL. When determining the difference absorption spectra by use of this reference absorption spectrum, it is possible to reduce the influences of the change in scattering at the background structure, and a spectrum change caused by fluctuations among days of the in-vivo components.

What is claimed is:

1. A method of non-invasively determining a concentration of an in-vivo component of a subject by use of a plurality of difference absorption spectra, wherein the plurality of said difference absorption spectra are defined by a difference between each one of a plurality of first near-infrared absorption spectra of a simulated living body and a first reference absorption spectrum selected from the plurality of the first near-infrared absorption spectra of the simulated living body respectively and wherein the plurality of said difference absorption spectra are predetermined according to a light propagation simulation respectively, which is defined as a method of analyzing a light propagation in the simulated living body, by using optical characteristics including absorption coefficient "$\mu_a$", scattering coefficient "$\mu_s$", refraction index "n", and anisotropic scattering parameter "g" of each epidermis layer, dermis layer and hypodermis layer, said method comprising steps of:

measuring a second near-infrared absorption spectra of the subject;

determining a second reference absorption spectrum by use of the second near-infrared absorption spectra;

synthesizing the plurality of said difference absorption spectra with the second reference absorption spectrum respectively, thereby obtaining a plurality of synthetic absorption spectra;

performing a multivariate analysis with use of the plurality of said synthetic absorption spectra to prepare a calibration curve;

measuring a third near-infrared absorption spectrum of the subject; and determining the concentration of said in-vivo component of the subject by use of the third near-infrared absorption spectrum of the subject and said calibration curve.

2. The method as set forth in claim 1, wherein said in-vivo component is glucose.

3. The method as set forth in claim 1, wherein said light propagation simulation is a Monte Carlo simulation.

* * * * *